| United States Patent [19] | [11] Patent Number: 4,677,125 |
|---|---|
| Teranishi et al. | [45] Date of Patent: Jun. 30, 1987 |

[54] PHOSPHORUS-CONTAINING PEPTIDE DERIVATIVES

[75] Inventors: Masayuki Teranishi; Mitsuru Takahashi; Hisayo Nomoto; Hiroshi Kase, all of Tokyo; Katsuichi Shuto, Shizuoka; Kazuhiro Kubo, Shizuoka; Akira Karasawa, Shizuoka, all of Japan

[73] Assignee: Kyowa Hakko Kogyo Co., Ltd., Tokyo, Japan

[21] Appl. No.: 902,109

[22] Filed: Aug. 29, 1986

Related U.S. Application Data

[63] Continuation of Ser. No. 807,205, Dec. 11, 1985, abandoned, which is a continuation of Ser. No. 692,313, Jan. 16, 1985, abandoned, which is a continuation of Ser. No. 533,658, Sep. 19, 1983, abandoned.

[30] Foreign Application Priority Data

Sep. 17, 1982 [JP]  Japan ................................ 57-161788
Sep. 17, 1982 [JP]  Japan ................................ 57-161789

[51] Int. Cl.⁴ ...................... A61K 37/02; C07K 5/08
[52] U.S. Cl. ............................................ 514/7; 530/331
[58] Field of Search ............................... 514/7; 530/331

[56] References Cited

U.S. PATENT DOCUMENTS

| 4,016,148 | 4/1977 | Atherton et al. ............ 260/112.5 R |
|---|---|---|
| 4,100,275 | 7/1978 | Atherton et al. .................... 424/177 |
| 4,127,649 | 11/1978 | Atherton et al. .................... 424/177 |
| 4,128,542 | 12/1978 | Atherton et al. ............ 260/112.5 R |
| 4,134,972 | 1/1979 | Atherton et al. .................... 424/177 |
| 4,143,134 | 3/1979 | Atherton et al. ............ 260/112.5 R |
| 4,250,085 | 2/1981 | Atherton et al. ............ 260/112.5 R |
| 4,331,591 | 5/1982 | Baylis ............................ 260/112.5 R |
| 4,522,812 | 6/1985 | Koguchi et al. ........................ 514/7 |

FOREIGN PATENT DOCUMENTS

| 0342192 | 3/1978 | Austria . |
|---|---|---|
| 0002822 | 7/1979 | European Pat. Off. . |
| 0061172 | 9/1982 | European Pat. Off. . |
| 2721761 | 12/1977 | Fed. Rep. of Germany ... 260/112.5 R |
| 2730524 | 1/1978 | Fed. Rep. of Germany . |
| 2732454 | 1/1978 | Fed. Rep. of Germany . |
| 2855786 | 7/1979 | Fed. Rep. of Germany . |
| 1533239 | 11/1978 | United Kingdom . |
| 1533240 | 11/1978 | United Kingdom . |
| 2030148 | 4/1980 | United Kingdom . |
| 1577232 | 10/1980 | United Kingdom ......... 260/112.5 R |
| 1,585,275 | 2/1981 | United Kingdom ......... 260/112.5 R |

*Primary Examiner*—Delbert R. Phillips
*Attorney, Agent, or Firm*—Fitzpatrick, Cella, Harper & Scinto

[57] ABSTRACT

Phosphorus-containing oligopeptide derivatives are prepared by synthetic methods. The compounds exhibit angiotensin converting enzyme-inhibiting action and are, therefore, useful as anti-hypertensive agents.

8 Claims, No Drawings

PHOSPHORUS-CONTAINING PEPTIDE DERIVATIVES

This application is a continuation of application Ser. No. 807,205 filed Dec. 11, 1985, now abandoned, which is a continuation of application Ser. No. 692,313 filed Jan. 16, 1985, now abandoned, which is a continuation of application Ser. No. 533,658, filed Sept. 19, 1983, now abandoned.

BACKGROUND OF THE INVENTION

The present invention pertains to phosphorus-containing oligopeptide derivatives which exhibit an angiotensin converting enzyme-inhibiting action and, thus, anti-hypentensive activity.

Heretofore, compounds typically represented by the formula:

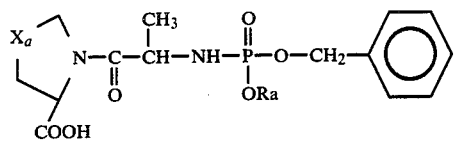

wherein $X_a$ is $CH_2$ or S, and Ra is hydrogen or benzyl, etc., have been known as phosphorus-containing peptide compounds having an angiotensin converting enzyme-inhibiting action (EP No. 0009 183 A1).

Compounds comparatively similar to the compounds of the present invention have been disclosed to have antibacterial activity in, e.g. GB No. 2030148A and Austrian Pat. No. 342192. These compounds are represented, for example, by the formula:

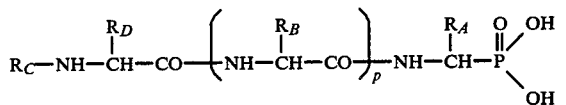

wherein $R_A$ is hydrogen, methyl, hydroxymethyl, or mono-, di- or tri-halomethyl; $R_B$ is an α-amino acid residual group, etc.; $R_C$ is lower alkyl, lower cycloalkyl, lower alkenyl, aryl or aralkyl; $R_D$ is hydrogen or lower alkyl; and p is 1, 2 or 3. However, there is no suggestion in the literature that the compounds have an angiotensin converting enzyme-inhibiting action or hypotensive activity which is pharmacologically distinct from antibacterial activity.

Furthermore, certain phosphorus-containing oligopeptides which have an angiotensin converting enzyme-inhibiting activity and anti-hypertensive action are disclosed in commonly owned EP No. 0061172 A1.

However, new and better anti-hypertensive agents are in demand and, in this regard, novel phosphorus-containing oligopeptides of the present invention have been synthesized which exhibit enhanced angiotensin converting enzyme-inhibiting action and, thus, anti-hypertensive activity.

DESCRIPTION OF THE INVENTION

The present invention pertains to phosphorus-containing peptide derivatives represented by the formula [I].

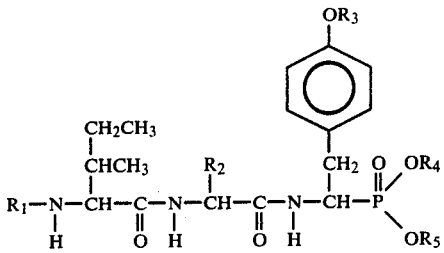

wherein $R_1$ is hydrogen, lower alkyl, lower alkoxycarbonyl, aralkyloxycarbonyl or

wherein $R_6$ is hydrogen, alkyl having 1 to 17 carbon atoms, unsubstituted or substituted aryl wherein the substituent is selected from lower alkyl, lower alkoxy and halogen, unsubstituted or substituted aralkyl wherein the substituent is selected from lower alkyl, lower alkoxy and halogen, or cycloalkyl having 5 or 6 carbon atoms; $R_2$ is hydrogen, unsubstituted or substituted lower alkyl wherein the substituent is selected from amino, mercapto, lower alkylthio, carboxyl, hydroxyl, guanidino and imidazolyl, unsubstituted or substituted aryl wherein the substituent is selected from amino, hydroxyl, lower alkoxy, aralkyloxy, lower alkyl, halogen and nitro, unsubstituted or substituted aralkyl wherein the substituent is selected from amino, lower alkyl, halogen and nitro, or

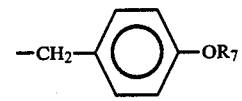

wherein $R_7$ has the same meaning as $R_3$; $R_3$ is hydrogen, lower alkyl, unsubstituted or substituted aralkyl wherein the substituent has the same meaning as in $R_6$, $R_8$—CO— wherein $R_8$ has the same meaning as $R_6$, $R_9$—O—CO— wherein $R_9$ is lower alkyl, unsubstituted or substituted aryl wherein the substituent has the same meaning as in $R_6$, unsubstituted or substituted aralkyl wherein the substituent has the same meaning as in $R_6$, or $R_9$NHCO— wherein $R_9$ has the same meaning as defined above; and $R_4$ and $R_5$ are the same or different, and are hydrogens, alkyls having 1 to 18 carbon atoms, unsubstituted or substituted aryl wherein the substituent has the same meaning as $R_6$, unsubstituted or substituted aralkyl wherein the substituent has the same meaning as in $R_6$, —$(CH_2CH_2O)_mCH_3$ wherein m is an integer of 1-4, or —$CH[CH_2OCO(CH_2)_nCH_3]_2$ wherein n is 0 or an integer of 1-10, and pharmacologically acceptable salts thereof.

Compounds of the formula [I] are hereinafter referred to as Compound [I] and compounds of other formula numbers are hereinafter referred to in similar fashion.

In the definition of $R_1$ in the general formula [I], lower alkyl means straight or branched alkyls having 1 to 6 carbon atoms, for example, methyl, ethyl, n-propyl, i-propyl, n-butyl, i-butyl, t-butyl, s-butyl, pentyl, hexyl, etc. Preferable lower alkyls are methyl, ethyl, n-propyl, i-propyl, etc. Similarly, lower alkoxycarbonyl means straight or branched alkoxycarbonyls having 2 to 7 carbon atoms. Preferable examples are ethoxycarbonyl, propoxycarbonyl and t-butoxycarbonyl. Furthermore, in the definition of $R_1$, aralkyloxycarbonyl means those having phenyl, naphthyl, biphenyl, etc. as the aryl part and alkyl having 1 to 3 carbon atoms as the alkyl part. Preferable examples are benzyloxycarbonyl and phenethyloxycarbonyl.

In the definition of $R_6$, the alkyl having 1 to 17 carbon atoms may be straight or branched and includes, for example, methyl, ethyl, n-propyl, i-propyl, n-butyl, i-butyl, t-butyl, s-butyl, pentyl, hexyl, octyl, dodecyl and heptadecyl. In the same definition, the aryl of unsubstituted or substituted aryl means phenyl, naphthyl, biphenyl, etc. In the definition of the substituent, the lower alkyl and the lower alkoxy means those having 1 to 3 carbon atoms respectively, and the halogen is exemplified by chlorine, bromine, etc. In the definition of $R_6$, the aryl part of the aralkyl of unsubstituted or substituted aralkyl means phenyl, naphthyl, biphenyl, etc., and the alkyl part means alkyl having 1 to 3 carbon atoms. Substituents similar to those of the substituted aryl are used as a substituent for the substituted aralkyl. For example, benzyl, phenethyl, 3-phenylpropyl, trityl, etc. may be used.

In the definition of $R_6$, the cycloalkyl having 5 to 6 carbon atoms means cyclopentyl or cyclohexyl. Preferable examples of

are formyl, acetyl, propionyl, pivaloyl, stearoyl, benzoyl and phenylacetyl.

In the definition of $R_2$, the lower alkyl of unsubstituted or substituted lower alkyl means straight or branched alkyls having 1 to 6 carbon atoms. In the definition of the substituent, the lower alkylthio means those having 1 to 3 carbon atoms. The aryl of unsubstituted or substituted aryl in the definition of $R_2$ includes phenyl, naphthyl, biphenyl, etc. In the definition of the substituent, the lower alkoxy means those having 1 to 3 carbon atoms; the aralkyloxy means those having phenyl, naphthyl, biphenyl or the like as the aryl part and an alkyl having 1 to 3 carbon atoms as the alkyl part; the lower alkyl means those having 1 to 3 carbon atoms; and the halogen means chlorine, bromine, etc. In the definition of $R_2$, the aralkyl of the unsubstituted or substituted aralkyl means those having phenyl, naphthyl, biphenyl, or the like as the aryl part and an alkyl having 1 to 3 carbon atoms as the alkyl part. In the definition of the substituent, the lower alkyl means those having 1 to 3 carbon atoms and the halogen means chlorine, bromine, etc. $R_2$ is a part corresponding to the side chain of the ordinary amino acid and preferably includes methyl (alanine), i-propyl (valine), 1-methylpropyl (isoleucine), 2-methylpropyl (leucine), 3-aminopropyl (ornithine), 4-aminobutyl (lysine), hydroxymethyl (serine), 1-hydroxyethyl (threonine), 2-hydroxyethyl (homoserine), mercaptomethyl (cysteine), 2-methylthioethyl (methionine), carboxymethyl (asparitc acid), 2-carboxyethyl (glutamic acid), benzyl (phenylalanine),

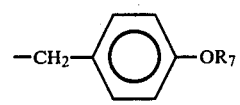

(tyrosine and derivatives thereof), etc., among which methyl, i-propyl, 1-methylpropyl, benzyl, 4-aminobutyl,

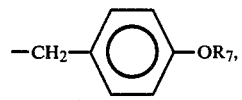

etc. are especially preferable.

In the definition of $R_3$ and $R_7$, the lower alkyl and the unsubstituted or substituted aralkyl have the same meanings as defined above with respect to $R_1$. The lower alkyl includes preferably methyl, ethyl, etc., and the unsubstituted or substituted aralkyl includes preferably benzyl, etc. Preferable examples of

are acetyl, propionyl, n-hexanoyl, lauroyl and stearoyl. The respective groups of $R_9$ have the same meanings as defined above with respect to $R_1$. Preferable examples of

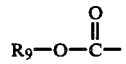

are ethoxycarbonyl, t-butoxycarbonyl and benzyloxycarbonyl.

In the definition of $R_4$ and $R_5$, the alkyl having 1 to 18 carbon atoms may be straight or branched, and includes, for example, methyl, ethyl, n-propyl, i-propyl, n-butyl, t-butyl, 1-methylpropyl, pentyl, hexyl, octyl, dodecyl and octadecyl, among which methyl, ethyl, n-propyl, i-propyl, n-butyl, dodecyl, octadecyl, etc. are preferable. In the definition of $R_4$ and $R_5$, the unsubstituted or substituted aryl and the unsubstituted or substituted aralkyl have the same meanings as defined above with respect to $R_6$, respectively. Preferable groups with respect to m or n in $R_4$ and $R_5$ are $-(CH_2CH_2O)_4CH_3$, and $-CH[CH_2OCO(CH_2)_{10}CH_3]_2$.

When Compound [I] is an acidic compound, a base addition salt can be formed, and when it is a basic compound, an acid addition salt can be formed. The salt includes ammonium salts, alkali metal salts such as lithium, sodium and potassium salts, alkaline earth metal salts such as calcium and magnesium salts, salts with organic bases such as triethylamine, morpholine, piperidine, dicyclohexylamine, etc., and salts with amino acids such as arginine, lysine, etc. Furthermore, salts with inorganic or organic acids such as hydrochloride, hydrobromide, sulfate, nitrate, formate, acetate, benzoate, maleate, fumarate, succinate, tartrate, citrate, oxalate, methanesulfonate, toluenesulfonate, aspartate, glutamate, etc. can be prepared.

Pharmacologically acceptable non-toxic salts are preferable, but other salts are also usable in the isolation and purification of products. These salts can be prepared according to the ordinary procedure, for example, by reacting Compound [I] with an appropriate base or acid in at least an equivalent amount to Compound [I] in a solvent such as water or alcohol and removing the solvent therefrom by evaporation or freeze drying, or by exchanging the cation of a salt of Compound [I] with another cation on an appropriate ion exchange resin.

In the general formula [I], the carbon atoms to which $CH_3CH_2CH(CH_3)$—, $R_2$ in case of being not hydrogen and

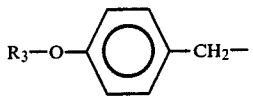

are bonded are asymmetric carbons.

According to the present invention, racemates, enantiomers or diasteromers can be obtained as products by proper selection of starting materials and intermediates. Diastereomer mixtures as obtained can be separated by the ordinary chromatography or fractional crystallization. Compound [I] whose configuration of asymmetric carbon is either R or S can attain the purpose of the present invention, but preferably, the compounds in which the carbons to which $CH_3CH_2CH(CH_3)$— and $R_2$ are bonded have each an S— configuration, and the carbon to which

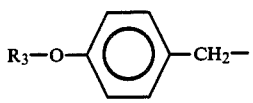

is bonded has an R— configuration are selected.

Process for preparing Compound [I] is described below as grouped into two procedures, i.e. general synthetic procedure and specific synthetic procedure.

For simplification, the general formula [I] is hereinafter abbreviated as follows, and other formulae will be also likewise abbreviated:

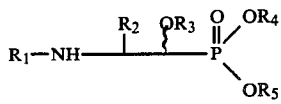

General synthetic procedure 1

Compounds of general formula [I] wherein $R_1$, $R_3$, $R_4$ and $R_5$ are not hydrogens, and hydroxyl, amino, guanidino, carboxyl, mercapto or imidazolyl in $R_2$, if any, is protected by a protective group usually used in the peptide chemistry (which are hereinafter referred to as Compound [I']) can be synthesized according to the following steps:

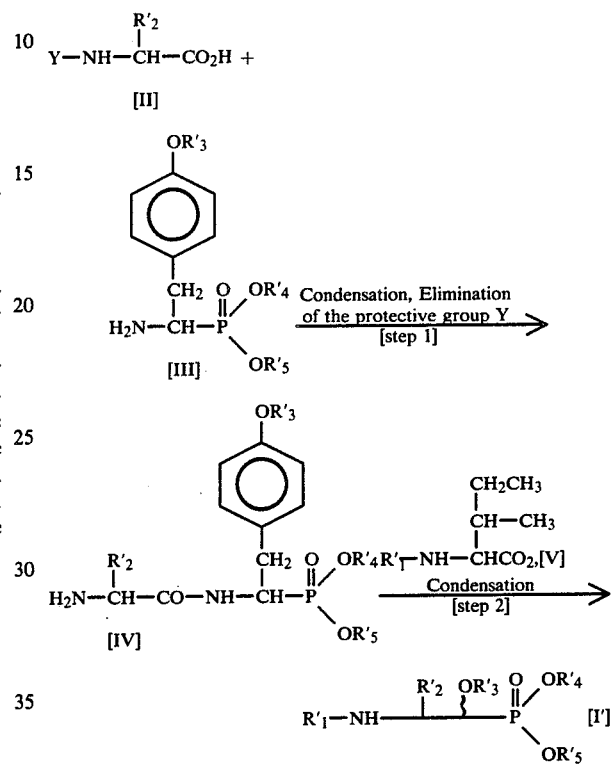

(wherein Y is an amino-protecting group; $R'_2$ has the same definition as $R_2$, or when $R_2$ contains hydroxyl, amino, guanidino, carboxyl, mercapto or imidazolyl, $R'_2$ is the same as $R_2$ wherein these groups are protected by a protective group usually used in the peptide chemistry; and $R'_1$, $R'_3$, $R'_4$ and $R'_5$ are respectively the same as $R_1$, $R_3$, $R_4$ and $R_5$ excluding hydrogen).

General synthetic procedure 2

Compounds of general formula [I] wherein at least one of $R_1$, $R_3$, $R_4$ and $R_5$ are hydrogens, or compounds of general formula [I'] wherein $R'_2$ is deprotected to $R_2$ can be synthesized according to the following steps:

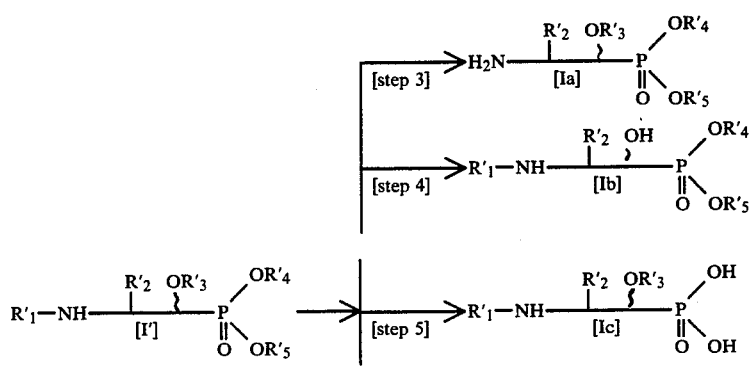

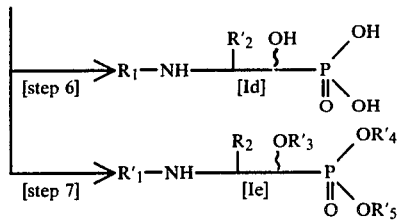

(wherein R'₁, R'₂, R'₃, R'₄, R'₅ and R₂ have the same meanings as defined above).

The respective steps are explained below.

[Step 1]

A patent application relating to an invention of Compound [III] has been filed (EP No. 0061172 A1), and the compound can also be synthesized through a combination of known processes [reference: M. J. Stringer et al, Chem. Biol, Interactions, 9, 411 (1974), Z. H. Kudzin and A. Kotynski, Synthesis, 1028 (1980)].

The other starting material, Compound [II] is a protective amino acid usually used in the field of peptide synthesis chemistry.

Condensation of Compounds [II] and [III] can be carried out with a condensing agent usually used in the peptide synthesis. For example, N,N'-dicyclohexylcarbodiimide (hereinafter referred to as "DCC"), and DCC in combination with 1-hydroxybenzotriazole or N-hydroxysuccinimide can be used. Further, a mixed acid anhydride process using ethyl chlorocarbonate, isobutyl chlorocarbonate, etc. and an active esterification process through p-nitrophenyl ester, etc. can also be used. The reaction solvent includes a solvent usually used in the peptide synthesis, for example, tetrahydrofuran, dioxane, chloroform, dichloromethane, ethyl acetate, N,N-dimethylformamide, etc. and a mixture thereof. The reaction is carried out usually in the range of $-30°$ to $+30°$ C.

After the condensation of Compounds [II] and [III], the amino-protecting group Y is removed according to the procedure usually used in the peptide synthesis to obtain Compound [IV]. For example, when Y is a t-butoxycarbonyl group, treatment with an acid such as hydrogen chloride can produce Compound [IV], and when Y is a benzyloxycarbonyl group, catalytic reduction can produce Compound [IV].

When Compound [III] is an optically inactive compound and Compound [II] is an optically active compound, Compound [IV] can be separated as a diastereomer.

Compound [IV] can also be isolated as an acid addition salt such as hydrochloride, hydrobromide, etc., and in that case the acid addition salt as such can be used as a starting material for Step 2.

Some of Compound [IV] are disclosed in EP No. 0061172 A1.

[Step 2]

Compound [I'] can be obtained through reactions and treatments basically similar to those of Step 1. That is, the desired compound can be obtained by reaction of Compound [IV] obtained by the process of Step 1 with Compound [V], using a condensing agent usually used in the field of peptide synthesis chemistry as shown in Step 1 and by treatment under the same conditions as in Step 1.

[Step 3]

Compound [Ia] can be obtained by synthesizing Compound [I'] whose R'₁ is a group used as an amino-protective group in the ordinary peptide synthesis according to the Steps 1 and 2, and then removing R'₁ therefrom. For example, when R'₁ is a t-butoxycarbonyl group, Compound [Ia] can be obtained by treatment with an acid such as hydrogen chloride, and when R'₁ is a benzyloxycarbonyl group, Compound [Ia] can be obtained by catalytic hydrogenation.

[Step 4]

Compound [Ib] can be obtained by catalytic hydrogenation of Compound [I'] whose R'₃ is benzyl in the presence of a metallic catalyst. As the catalyst, palladium carbon, palladium black, etc. are preferable. An alcohol such as methanol, ethanol, etc., an ether such as tetrahydrofuran, dioxane, etc., N,N-dimethylformamide, acetic acid, hydrochloric acid, water, etc. alone or in combination are used as the solvent. Reaction time depends upon the kind of compound, hydrogen pressure, temperature and the kind of solvent, but usually is 3 to 24 hours.

[Step 5]

Compound [Ic] can be obtained by reacting one mole of Compound [I'] whose R'₄ and R'₅ are lower alkyls such as methyl and ethyl with 2 to 3 moles of trimethylsilyl bromide at room temperature and then by treating the product with water or an alcohol. In the case of Compound [Ic] whose R'₁ and R'₃ are alkyls or acyls, only R'₄ and R'₅ can be selectively converted to hydrogens by the reaction. Solvent for use in the reaction includes a halogenated hydrocarbon such as chloroform, dichloromethane, carbon tetrachloride, dichloroethane, etc., acetonitrile, nitromethane, etc. Reaction time is usually 4 to 15 hours.

[Step 6]

Compound [Id] can be obtained by treating Compound [I'] whose R'₃ is benzyl, trityl, t-butyl, benzyloxycarbonyl or t-butoxycarbonyl and whose R'₄ and R'₅ are lower alkyls such as methyl, ethyl, etc. with an acetic acid solution of hydrogen bromide. In the case of Compound [I'] whose R'₁ is alkyl or acyl, R'₃, R'₄ and R'₅ can be converted to hydrogens without reaction of R'₁, and in the case of Compound [I'] whose R'₁ is t-butoxycarbonyl or benzyloxycarbonyl, all of R'₁, R'₃, R'₄ and R'₅ can be converted to hydrogens. The reaction is completed usually in 5 to 15 hours at room temperature. When R₁ is hydrogen or alkyl, Compound [Id] can be isolated as a hydrobromide, and it can be desalted by treating it with propylene oxide in an alcohol, or by treating its aqueous solution with silver oxide.

[Step 7]

The protective group in R'₂ can be removed according to a method generally used in the peptide synthesis. Some kinds of protective groups are removed under the conditions of the above Steps 3 to 6. For example, an amino-protecting group and a protective group of phenolic hydroxyl in $R'_2$ can be removed respectively in Step 3 and in Step 4. Particularly, when $R_2$ is

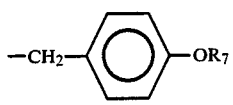

and $R_7$ is $R'_3$, $R_7$ is removed in Step 4.

By subjecting Compounds [I'a], [I'b], [I'c] and [I'd] to the same reaction as in Step 7, $R'_2$ can be converted to $R_2$. Furthermore, by subjecting Compound [Ie] to the same reaction as in Step 3, 4, 5 or 6, at least one of $R'_1$, $R'_3$, $R'_4$ and $R'_5$ can be converted to hydrogen.

Compound [I] of the present invention having many substituents, i.e. $R_1$, $R_2$, $R_3$, $R_4$ and $R_5$ can be synthesized according to the general synthesis procedure, Step 1 to Step 7 alone or in combination. However, when specific groups of $R_1$ to $R_5$ are fixed and the remaining groups are varied, the following specific synthesis procedures 1 to 3 [steps 8, 8', 9, 9', 9'', 10 and 11] are more efficient.

Specific synthetic procedure 1

Synthesis of Compound [I'] whose $R'_1$ is of various types:

(wherein $R'''_1$ is $R_1$ excluding hydrogen and lower alkyl; $R''_3$ means lower alkyl, or unsubstituted or substituted aralkyl in the definition of $R_3$; and $R'_2$, $R'_4$, $R'_5$, $R_7$, $R_8$ and X have the same meanings as defined above).

Specific synthetic procedure 3

Synthesis of Compound [I'] whose $R'_4$ and $R'_5$ are of various types:

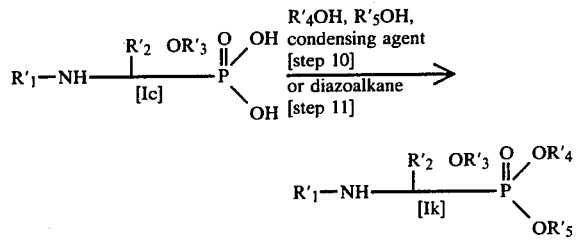

(wherein $R'_1$, $R'_2$, $R'_3$, $R'_4$ and $R'_5$ have the same meanings as defined above).

The respective steps are explained below:

[Steps 8 and 8']

Compound [If] can be obtained by reacting Compound [Ia] with a reactive derivative of a carboxylic acid represented by

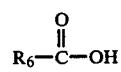

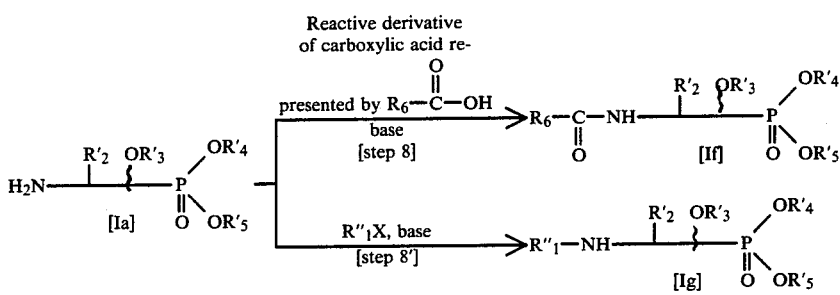

(wherein $R''_1$ means lower alkoxycarbonyl or aralkyloxycarbonyl in $R_1$; $R'_2$, $R'_3$, $R'_4$, $R'_5$ and $R_6$ have the same meanings as defined above; and X is halogen.

Specific synthetic procedure 2

Synthesis of Compound [I'] whose $R'_3$ is of various types:

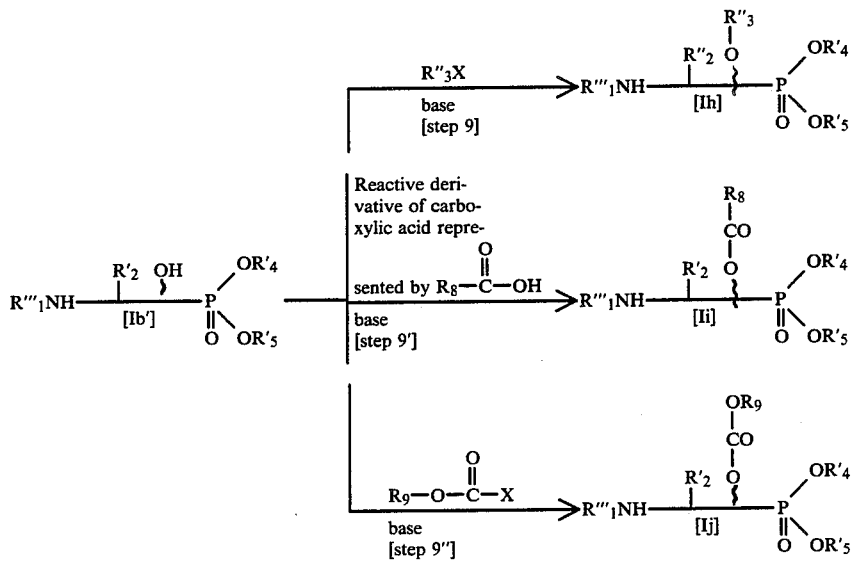

in the presence of a base. The reactive derivative for use in this step includes an acid halide (for example, acid chloride and acid bromide), an acid anhydride (including a product from

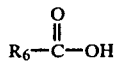

and DCC), a mixed acid anhydride (for example, mixed acid anhydride with alkyl chlorocarbonate), an active ester (p-nitrophenyl ester, etc.), etc.

The base is necessary for neutralization when an acid is formed by the reaction or when Compound [Ia] is used as an acid salt. As the base, triethylamine, pyridine, 4-dimethylaminopyridine, N-methylmorpholine, sodium hydroxide, sodium hydrogen carbonate, etc. can be used. The reaction solvent for use in this step includes chloroform, dichloromethane, ethyl acetate, tetrahydrofuran, pyridine, N,N-dimethylformamide, water, etc. alone or in combination. Reaction is carried out at 0° C. to room temperature and is usually complete in 30 minutes to 15 hours.

Compound [Ig] can be obtained by reacting Compound [Ia] with $R''_1X$ in the presence of a base. $R''_1X$ is exemplified by alkyl chlorocarbonate, aralkyl chlorocarbonate, etc. The base, reaction solvent and reaction conditions are the same as in Step 8.

[Steps 9, 9′ and 9″]

Compound [Ih] can be obtained by reacting Compound [Ib′] with $R''_3X$ in the presence of a base. The base, reaction solvent and reaction conditions are the same as in Step 8.

Compound [Ii] can be obtained by reacting Compound [Ib′] with a reactive derivative of a carboxylic acid represented by

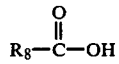

in the presence of a base. The reactive derivative, base, reaction solvent and reaction conditions are the same as in Step 8.

Compound [Ij] can be obtained by reacting Compound [Ib] with

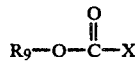

in the presence of a base. The base, reaction solvent and reaction conditions are the same as in Step 8.

In the above procedure, when a compound represented by the general formula:

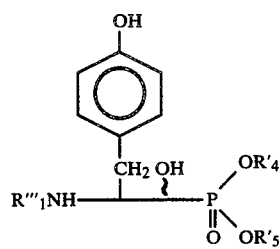

(wherein $R'''_1$, $R'_4$ and $R'_5$ have the same meanings as defined above) is selected, the both hydroxyls are simultaneously converted.

[Step 10]

Compound [Ik] can be obtained by esterifying Compound [Ic] with a condensing agent such as DCC, 2,4,6,-triisopropylbenzenesulfonyl chloride, etc., and an alcohol ($R'_4OH$ or $R'_5OH$) in the presence of a base. When two moles or more of the condensing agent and the alcohol are used respectively for one mole of Compound [Ic], Compound [Ik] having the same $R'_4$ and $R'_5$ can be obtained. When one mole of the condensing agent and one mole of alcohol ($R'_4OH$) is used, monoester can be obtained. When the monoester is further reacted with the condensing agent and an alcohol ($R'_5OH$), Compound [Ik] having different $R'_4$ and $R'_5$ can be obtained. The base for use in the reaction is pyridine or 4-dimethylaminopyridine. The reaction solvent for use includes N,N-dimethylformamide, pyridine, tetrahydrofuran, chloroform, etc. alone or in combination. Reaction is carried out usually at room temperature and is complete in a few hours to one day.

[Step 11]

Compound [Ik] having the same $R'_4$ $R'_5$ can also be obtained by reacting Compound [Ic] with diazoalkane. For example, a dimethyl ester derivative can be obtained by reacting Compound [Ic] with diazomethane in excess in ether or N,N-dimethylformamide at 0° C. for 15 minutes to 2 hours.

When it is desired to convert $R'_2$ to $R_2$ in the specific synthetic procedures 1 to 3, the purpose is attained by conducting the same treatment as in Step 7.

Certain specific embodiments of the invention are illustrated by the following representative Examples.

EXAMPLE 1

Diethyl ester of N-(N-t-butoxycarbonyl-L-isoleucyl-O-benzyl-L-tyrosyl)-(R)-(−)-1-amino-2-(4-benzyloxyphenyl)ethylphosphonic acid (1)

At first, 0.97 g (4.2 m moles) of N-t-butoxycarbonyl-L-isoleucine, 2.61 g (4.0 m moles) of diethyl ester hydrochloride of N-(O-benzyl-L-tyrosyl)-(R)-(−)-1-amino-2-(4-benzyloxyphenyl)ethylphosphonic acid 46a (see Reference Example 1), and 0.57 g (4.2 m moles) of 1-hydroxybenzotriazole were dissolved in 30 ml of tetrahydrofuran (hereinafter referred to as THF), and the solution was cooled to about −10° C. on dry ice-ice bath while stirring the solution. Then, 0.462 ml (4.2 m moles) of N-methylmorpholine and then a solution of 0.87 g (4.2 m moles) of DCC in 10 ml of THF were added dropwise to the solution. Temperature of the reaction mixture was elevated to 0° C. over about 2 hours, and then the reaction mixture was stirred at room temperature overnight. Deposited N,N′-dicyclohexylurea was removed by filtration, and 100 ml of ethyl acetate was added to the filtrate and then the mixture was washed with an aqueous 5% sodium hydrogen carbonate solution, an aqueous 5% citric acid solution and then an aqueous saturated sodium chloride solution (3×30 ml each) and dried over anhydrous sodium sulfate. The solvent was removed therefrom under reduced pressure to obtain a light yellow solid. The solid was purified by silica gel column chromatography (chloroform:acetone=95:5), and the solvent was removed therefrom under reduced pressure to obtain 3.11 g of the captioned compound in a white powdery state (94%).

| Elemental analysis (%): as $C_{46}H_{60}N_3O_9P$ | | |
|---|---|---|
| | Calculated | Found |
| C | 66.57 | 66.72 |
| H | 7.29 | 7.32 |
| N | 5.06 | 5.06 |

$[\alpha]_D^{22} = -43.9°$; (C=1.0, methanol).
$^1$H—NMR (CDCl$_3$): δ7.35(m, 10H), 7.2–6.6(m, 8H), 4.99(s, 2H), 4.95(s, 2H), 4.9–4.4(m, 2H), 4.3–3.7(m, 5H), 3.3–2.6(m, 4H), 1.9–1.0(m, 3H), 1.29(t, 3H, J=7.1 Hz), 1.25 (t, 3H, J=7.1 Hz), 1.0–0.6(m, 6H).
MS (30 eV): m/Z 829 (M+).
IR (KBr): 3280, 2960, 1690, 1645, 1510, 1240, 1170, 1040, 1020, 960 cm$^{-1}$.

EXAMPLE 2

Diethyl ester hydrochloride of N-(N-L-isoleucyl-O-benzyl-L-tyrosyl)-(R)-(−)-1-amino-2-(4-benzyloxyphenyl)ethylphosphonic acid (2):

At first, 19.2 ml of a solution of 2.6N hydrogen chloride in ethyl acetate was added to a solution of 2.07 g the compound 1 in 10 ml of ethyl acetate, and the mixture was stirred at room temperature for one hour. The solvent and excess hydrogen chloride were removed therefrom under reduced pressure and 10 ml of ethyl ether was added to the residue, and a white solid was obtained by trituration of the mixture. The solid was washed with ethyl ether (3×5 ml) and dried under reduced pressure to obtain 1.77 g of the captioned compound in a white powdery state (89%).

| Elemental analysis (%): as $C_{41}H_{53}Cl\ N_3O_7P$ | | |
|---|---|---|
| | Calculated | Found |
| C | 64.26 | 64.15 |
| H | 6.97 | 6.97 |
| N | 5.48 | 5.50 |

$[\alpha]_D^{19} = -8.8°$; (C=0.50, methanol).
$^1$H—NMR (CDCl$_3$): δ7.34(m, 10H), 7.3–6.65(m, 8H), 4.97(s, 4H), 4.85–4.3(m, 2H), 4.05(m, 4H), 3.25–2.55(m, 4H), 2.0–1.0(m, 3H), 1.31(t, 3H, J=7.3 Hz), 1.21(t, 3H, J=7.3 Hz), 1.0–0.4(m, 6H).
MS (20 eV): m/Z 729 (M+−HCl).

EXAMPLE 3

Diethyl ester hydrochloride of N-(L-isoleucyl-L-tyrosyl)-(R)-(−)-1-amino-2-(4-methoxyphenyl)ethylphosphonic acid (3):

White powdery material was obtained from N-t-butoxycarbonyl-L-isoleucine and diethyl ester hydrochloride of N-L-tyrosyl-(R)-(−)-1-amino-2-(4-methoxyphenyl)ethylphosphonic acid 47a (see Reference Example 2) in the same manner as in Example 1. The material was further treated in the same manner as in Example 2 to obtain the captioned compound in a white powdery state.
$[\alpha]_D^{25} = -10.5°$; (C=0.20, methanol).
MS (20 eV): m/Z 563 (M+−HCl).

EXAMPLE 4

Diethyl ester of N-(N-phenylacetyl-L-isoleucyl-O-benzyl-L-tyrosyl)-(R)-(−)-1-amino-2-(4-benzyloxyphenyl)ethylphosphonic acid (4):

A solution of 766 mg (1 m mole) of the compound 2 and 0.225 ml (2.05 m moles) of N-methylmorpholine in 40 ml of anhydrous chloroform was ice-cooled, and 0.123 ml (1.05 m moles) of phenylacetyl chloride was added thereto. The mixture was stirred for 5 hours. The reaction mixture was washed with an aqueous 5% sodium hydrogen carbonate solution, an aqueous 5% citric acid solution and then an aqueous saturated sodium chloride solution (2×25 ml each), and dried over anhydrous sodium sulfate, and the solvent was removed therefrom under reduced pressure to obtain 415 mg of a light yellow powder (49%). The powder was purified by silica gel column chromatography (chloroform:acetone=2:1) and the solvent was removed therefrom under reduced pressure to obtain the captioned compound in a white crystalline state.
Melting point: 161.5°–163° C.
$[\alpha]_D^{28} = -56.0°$ (C=0.50, N,N-dimethylformamide hereinafter referred to as DMF).

EXAMPLE 5

Diethyl ester of N-(N-benzoyl-L-isoleucyl-O-benzyl-L-tyrosyl)-(R)-(−)-1-amino-2-(4-benzyloxyphenyl)ethylphosphonic acid (5):

In the same manner as in Example 4, 1.08 g of the captioned compound in a white crystalline state was obtained from benzoyl chloride and the compound 2 (73%).
Melting point: 191.5°–193° C.

EXAMPLE 6

Diethyl ester of N-(N-formyl-L-isoleucyl-O-benzyl-L-tyrosyl)-(R)-(−)-1-amino-2-(4-benzyloxyphenyl)ethylphosphonic acid (6):

A solution in THF of 800 mg (1.04 m moles) of the compound 2, 69.2 μl (1.56 m moles) of formic acid and 170 μl (1.56 m moles) of N-methylmorpholine was ice-cooled, and a solution of 322 mg (1.56 m moles) of DCC in THF (5 ml) was added dropwise thereto. The mixture was stirred as such for 2 hours and further at room temperature overnight. Deposited N,N'-dicyclohexylurea was removed therefrom by filtration, and 30 ml of chloroform was added to the filtrate. The resulting homogeneous solution was washed with an aqueous 5% sodium hydrogen carbonate solution and then an aqueous saturated sodium chloride solution (2×20 ml each), and dried over anhydrous sodium sulfate. The solvent was removed therefrom under reduced pressure to obtain 600 mg of the captioned compound in a light yellow powdery state (76%).
$[\alpha]_D^{28} = -62.0°$; (C=0.20, DMF).
$^1$H—NMR (CDCl$_3$): δ8.11(s, 1H), 7.30(m, 10H), 7.3–6.7(m, 8H), 4.88(s, 2H), 4.83(s, 2H), 4.9–4.2(m, 2H), 4.2–3.7(m, 5H), 3.2–2.55(m, 4H), 1.9–1.0(m, 3H), 1.26(t, 3H, J=7 Hz), 1.23(t, 3H, J=7 Hz), 1.0–0.6(m, 6H).

EXAMPLE 7

Diethyl ester of N-(N-stearoyl-L-isoleucyl-O-benzyl-L-tyrosyl)-(R)-(−)-1-amino-2-(4-benzyloxyphenyl)ethylphosphonic acid (7):

In the same manner as in Example 6, 762 mg of the captioned compound in a light yellow powdery state was obtained from stearic acid and the compound 2 (77%).
$[\alpha]_D^{28} = -39.0°$; (C=0.20, DMF).

EXAMPLE 8

Diethyl ester of N-(N-formyl-L-isoleucyl-L-tyrosyl)-(R)-(−)-1-amino-2-(4-hydroxyphenyl)ethylphosphonic acid (8):

A suspension of 250 mg (0.33 m moles) of the compound 6 and 125 mg of 10% palladium-carbon in 5 ml of acetic acid was stirred in a hydrogen gas stream at room temperature for 8 hours. Insoluble matters were removed therefrom by filtration, and the solvent was removed from the filtrate under reduced pressure to obtain a white solid. The solid was recrystallized from methanol to obtain 157 mg of the captioned compound in a white crystalline state (82%).

Melting point: 253°–255° C.
$[\alpha]_D^{28} = -68.0°$; (C=0.20, DMF).
$^1$H—NMR (CD$_3$OD): $\delta$8.04(s, 1H), 7.15–6.6(m, 8H), 4.7–4.3(m, 2H), 4.3–3.9(m, 5H), 3.3–2.5(m, 4H), 1.9–1.0(m, 3H), 1.31(t, 6H, J=7.1 Hz), 1.0–0.6(m, 6H).

EXAMPLE 9

N-(N-phenylacetyl-L-isoleucyl-L-tyrosyl)-(R)-(−)-1-amino-2-(4-hydroxyphenyl)ethylphosphonic acid (9):

At first, 10 ml of a 25% hydrogen bromide solution in acetic acid was added to a solution of 451 mg (0.53 m moles) of the compound 4 and 1.15 ml of anisole in 5 ml of acetic acid, and the mixture was stirred at room temperature for 5 hours. Volatile matters were removed therefrom under reduced pressure, and 5 ml of ethyl ether was added to the residue. The mixture was triturated and supernatant was discarded. Solid obtained by 3 repetitions of this procedure were dried under reduced pressure to obtain 336 mg of a light yellow powder (100%). The powder was recrystallized from methanol-chloroform to obtain 256 mg of the captioned compound in a white crystalline state (79%).

Melting point: (233°–235° C.
$[\alpha]_D^\infty = -62.5°$; (C=0.20, DMF).
$^1$H—NMR (CD$_3$OD): $\delta$7.26(s, 5H), 7.2–6.5(m, 8H), 4.8–4.2(m, 2H), 4.08(d, 1H, J=8.1 Hz), 3.50(s, 2H), 3.3–2.4(m, 4H), 1.9–1.0(m, 3H), 1.0–0.5(m, 6H).

EXAMPLE 10

N-(N-benzoyl-L-isoleucyl-L-tyrosyl)-(R)-(−)-1-amino-2-(4-hydroxyphenyl)ethylphosphonic acid (10):

In the same manner as in Example 9, the captioned compound in a light yellow crystalline state was obtained from the compound 5.

Melting point: 240°–242.5° C.
$[\alpha]_D^{28} = -61.0°$; (C=0.20, DMF).
$^1$H—NMR (D$_2$O—NaOD): $\delta$7.9–7.4(m, 5H), 7.1–6.3(m, 8H), 4.56(m, 1H), 4.35(d, 1H, J=8.1 Hz), 4.07(m, 1H), 3.3–2.8(m, 2H), 2.8–2.3(m, 2H), 2.1–0.9(m, 3H), 1.0–0.6(m, 6H).

EXAMPLE 11

N-(N-formyl-L-isoleucyl-L-tyrosyl)-(R)-(−)-1-amino-2-(4-hydroxyphenyl)ethylphosphonic acid (11):

In the same manner as in Example 9, 231 mg of a light yellow solid was obtained from the compound 6 (98%), and recrystallized from methanol-chloroform to obtain the captioned compound in a light yellow crystalline state.

Melting point: >300° C. (turned brown at 230° C.).
$[\alpha]_D^{28} = -79.0°$; (C=0.20, DMF).
$^1$H—NMR (CD$_3$OD—DMSO—d$_6$): $\delta$8.05(s, 1H), 7.2–6.55(m, 8H), 3.2–2.5(m, 4H), 1.9–1.0(m, 3H), 1.0–0.6(m, 6H).

EXAMPLE 12

N-(N-stearoyl-L-isoleucyl-L-tyrosyl)-(R)-(−)-1-amino-2-(4-hydroxyphenyl)ethylphosphonic acid (12):

In the same manner as in Example 9, 340 mg of a light brown solid was obtained from the compound 7 (80%), and recrystallized from methanol to obtain 103 mg of the captioned compound in a light yellow crystalline state.

Melting point: 235.5°–238° C. (decomposed).
$[\alpha]_D^{28} = -40.0°$; (C=0.10, DMF).

EXAMPLE 13

N-(N-L-isoleucyl-L-tyrosyl)-(R)-(−)-1-amino-2-(4-hydroxyphenyl)ethylphosphonic acid (13):

At first, 5 ml of anisole and 5 ml of acetic acid were added to 1.92 g of the compound 1 to obtain a homogeneous solution, and 30 ml of a 25% hydrogen bromide solution in acetic acid was added thereto. The mixture was stirred at room temperature for 5 hours. Volatile matters were removed therefrom under reduced pressure to obtain 1.32 g of a light yellow powder. Then, 5 ml of propylene oxide was added dropwise to a homogeneous solution of 718 mg of the powder in 50 ml of ethanol. The resulting white precipitate was collected therefrom by filtration, washed with ethanol and then ethyl ether (2×3 ml each), and dried under reduced pressure to obtain 508 mg of the captioned compound in a white powdery state (82%).

Melting point: 300° C. or higher.
$[\alpha]_D^{24} = -93.1°$; (C=1.00, 1N NaOH).
$^1$H—NMR (D$_2$O—NaOD, DSS internal standard): $\delta$7.2–6.6(m, 8H), 4.48(m, 1H), 4.03(m, 1H), 3.3–2.8(m, 2H), 2.8–2.15(m, 2H), 1.9–1.0(m, 3H), 1.0–0.45(m, 6H).
IR (KBr): 3290, 2960, 1640, 1550, 1510, 1235, 1045, 1020 cm$^{-1}$.

EXAMPLE 14

Diethyl ester of N-(N-acetyl-D-isoleucyl-O-benzyl-L-tyrosyl)-(R)-(−)-1-amino-2-(4-benzyloxyphenyl)ethylphosphonic acid (14):

In the same manner as in Example 1, 712 mg of the captioned compound in a light yellow powdery state was obtained from N-acetyl-D-isoleucin and the compound 38a (see Reference Example 1) (92%).

Melting point: 151°–158° C.
$[\alpha]_D^{28} = -57.0°$; (C=0.20, DMF).

EXAMPLE 15

N-(N-acetyl-D-isoleucyl-L-tyrosyl)-(R)-(−)-1-amino-2-(4-hydroxyphenyl)ethylphosphonic acid (15):

In the same manner as in Example 9, 261 mg of the captioned compound in a white crystalline state was obtained from the compound 13 (75%).

Melting point: 222.5° C.
$[\alpha]_D^{28} = -85.0°$; (C=0.20, DMF).
$^1$H—NMR (CD$_3$OD): $\delta$7.25–6.5(m, 8H), 4.8–4.3(m, 2H), 3.92(d, 1H, J=8.3 Hz), 3.3–2.6(m, 4H), 2.01(s, 3H), 1.8–1.0(m, 3H), 1.0–0.4(m, 6H).

EXAMPLE 16

N-(N-acetyl-L-isoleucyl-L-tyrosyl)-(S)-(+)-1-amino-2-(4-hydroxyphenyl)ethylphosphonic acid (16):

Diethyl ester of N-(N-acetyl-L-isoleucyl-O-benzyl-L-tyrosyl)-(S)-(+)-1-amino-2-(4-benzyloxyphenyl)ethylphosphonic acid was obtained from N-acetyl-L-isoleucine and diethyl ester hydrochloride of N-(O-benzyl-L-tyrosyl)-(S)-(+)-1-amino-2-(4-benzyloxyphenyl)ethylphosphonic acid 46b (see Reference Example 1) in the same condensation procedure as in Example 1 (95%). The thus obtained compound was further treated in the same manner as in Example 9 to obtain an orange powder. The powder was recrystallized from methanol-water to obtain 250 mg of the captioned compound in a white crystalline state (60%).

Melting point: 277°–282° C. (decomposed).
$[\alpha]_D^{28} = +17.3°$; (C=0.358, methanol).
$^1$H—NMR (DMSO—d$_6$): δ7.2–6.4(m, 8H), 4.7–3.8(m, 3H), 3.3–2.5(m, 4H), 1.85(s, 3H), 1.85–0.9(m, 3H), 0.9–0.5(m, 6H).

EXAMPLE 17

Diethyl ester of N-(N-acetyl-L-isoleucyl-O-methyl-L-tyrosyl)-(R)-(−)-1-amino-2-(4-methoxyphenyl)-ethylphosphonic acid (17):

Diethyl ester of N-(N-acetyl-L-isoleucyl-L-tyrosyl)-(R)-(−)-1-amino-2-(4-hydroxyphenyl)ethylphosphonic acid was synthesized from N-acetyl-L-isoleucine and the compound 46a in the same condensation procedure as in Example 1 and then through the same reaction and treatment as in Example 8.

Then, 1.98 ml (1.98 m moles) of an aqueous 1N sodium hydroxide solution and then 0.168 ml (2.7 m moles) of methyl iodide were added to a solution of 532 mg (0.9 m moles) of the ester in 5 ml of methanol, and the mixture was stirred at room temperature for one day. Then, 50 ml of ethyl acetate was added to the reaction solution. The solution was washed with an aqueous 5% citric acid solution, an aqueous 5% sodium hydrogen carbonate solution and then an aqueous saturated sodium chloride solution (2×10 ml each), and dried over anhydrous sodium sulfate. The solvent was removed therefrom under reduced pressure to obtain 469 mg of a white solid (84%). The solid was recrystallized from chloroform-ethyl ether to obtain 430 mg of the captioned compound in a white crystalline state (77%).

Melting point: 225°–227° C.
$[\alpha]_D^{28} = -75.0°$; (C=0.208, DMF).
$^1$H—NMR (CDCl$_3$): δ7.2–6.6(m, 8H), 5.1–4.5(m, 2H), 4.4–3.8(m, 5H), 3.67(s, 3H), 3.64(s, 3H), 3.35–2.6(m, 4H), 1.97(s, 3H), 1.9–1.0(m, 3H), 1.27(t, 3H, J=7 Hz), 1.25 (t, 3H, J=7 Hz), 1.0–0.6(m, 6H).
MS (30 eV): m/Z 619 (M+).

EXAMPLE 18

Diethyl ester of N-(N-acetyl-L-isoleucyl-O-acetyl-L-tyrosyl)-(R)-(−)-1-amino-2-(4-acetoxyphenyl)ethylphosphonic acid (18):

At first, 35.6 μl (0.5 m mole) of acetyl chloride was added to a solution of 118 mg (0.2 m moles) of diethyl ester of N-(N-acetyl-L-isoleucyl-L-tyrosyl)-(R)-(−)-1-amino-2-(4-hydroxyphenyl)ethylphosphonic acid in 1 ml of pyridine, and the mixture was stirred at room temperature for 5 hours. Then, 1 ml of water was added to the reaction mixture to decompose excess acetyl chloride, and 50 ml of ethyl acetate and 20 ml of an aqueous saturated sodium chloride solution were added thereto to make the mixture distribute into two layers. The organic layer was collected, washed with an aqueous 5% citric acid solution, an aqueous 5% sodium hydrogen carbonate solution and then aqueous saturated sodium chloride solution (2×10 ml each), and dried over anhydrous sodium sulfate. The solvent was removed from the residue under reduced pressure to obtain 121 mg of a light yellow solid (90%). The solid was recrystallized from chloroform-ethyl ether to obtain 70 mg of the captioned compound in a white crystalline state (52%).

Melting point: 201°–202° C.

$[\alpha]_D^{28} = -68.8°$; (C=0.224, DMF).
$^1$H—NMR (CDCl$_3$): δ7.3–6.8(m, 8H), 5.0–4.4(m, 2H), 4.3–3.7(m, 5H), 3.3–2.6(m, 4H), 2.23(s, 6H), 1.94(s, 3H), 1.9–1.0(m, 3H), 1.27(t, 3H, J=7 Hz), 1.24(t, 3H, J=7 Hz), 1.0–0.6(m, 6H).
MS (30 eV): m/Z 675 (M+).

EXAMPLE 19

Diethyl ester of N-(N-acetyl-L-isoleucyl-O-benzoyl-L-tyrosyl)-(R)-(−)-1-amino-2-(4-benzoyloxyphenyl)ethylphosphonic acid (19):

In the same manner as in Example 18, 741 mg of a light yellow solid was obtained from benzoyl chloride and diethyl ester of N-(N-acetyl-L-isoleucyl-L-tyrosyl)-(R)-(−)-1-amino-2-(4-hydroxyphenyl)ethylphosphonic acid (93%). The solid was recrystallized from chloroform-ethyl ether to obtain 594 mg of the captioned compound in a white crystalline state (74%).

Melting point: 223°–225° C.
$[\alpha]_D^{28} = -65.5°$; (C=0.220, DMF).
$^1$H—NMR (CDCl$_3$): δ8.3–6.9(m, 18H), 5.2–4.5(M, 2H), 4.4–3.8(m, 5H), 3.5–2.6(m, 4H), 2.0–1.1(m, 3H), 1.97(s, 3H), 1.27(t, 6H, J=7 Hz), 1.0–0.6(m, 6H).
MS (30 eV): m/Z 799 (M+).

EXAMPLE 20

Diethyl ester of N-(N-acetyl-L-isoleucyl-O-pivaloyl-L-tyrosyl)-(R)-(−)-1-amino-2-(4-pivaloyloxyphenyl)-ethylphosphonic acid (20):

In the same manner as in Example 18, 734 mg of a light yellow solid was obtained from pivaloyl chloride and diethyl ester of N-(N-acetyl-L-isoleucyl-L-tyrosyl)-(R)-(−)-1-amino-2-(4-hydroxyphenyl)ethylphosphonic acid (100%). The solid was recrystallized from chloroform-ethyl acetate to obtain 603 mg of the captioned compound in a white crystalline state (82%).

Melting point: 262°–263° C.
$[\alpha]_D^{28} = -58.8°$; (C=0.204, DMF).
$^1$H—NMR (CDCl$_3$): δ7.3–6.8(m, 8H), 5.0–4.4(m, 2H), 4.3–3.8(m, 5H), 3.4–2.6(m, 4H), 1.93(s, 3H), 1.9–1.0(m, 9H), 1.30(s, 18H), 1.0–0.6(m, 6H).
MS (30 eV): m/Z 758 (M+).

EXAMPLE 21

Diethyl ester of N-{N-acetyl-L-isoleucyl-O-(3-phenylpropanoyl)-L-tyrosyl}-(R)-(−)-1-amino-2-{4-(3-phenyl-propanoyloxy)phenyl}ethylphosphonic acid (21):

At first, 557 mg (2.7 m moles) of DCC was added to a solution of 532 mg (0.9 m moles) of diethyl ester of N-(N-acetyl-L-isoleucyl-L-tyrosyl)-(R)-(−)-1-amino-2-(4-hydroxyphenyl)ethylphosphonic acid, 297 mg (1.98 m moles) of 3-phenylpropionic acid and 24 mg (0.2 m moles) of 4-dimethylaminopyridine in 5 ml of DMF, and the mixture was stirred at room temperature overnight. Deposited N,N′-dicyclohexylurea was removed therefrom by filtration, and 70 ml of ethyl acetate was added to the filtrate to obtain a homogeneous solution. The solution was washed with an aqueous 5% citric acid solution, an aqueous 5% sodium hydrogen carbonate solution and then an aqueous saturated sodium chloride solution (2×10 ml each), and dried over anhydrous sodium sulfate. The solvent was removed therefrom under reduced pressure to obtain a light yellow solid. The solid was purified by silica gel column chromatography (chloroform:acetone=7:3), and the solvent was removed therefrom under reduced pressure to obtain 436 mg of the captioned compound in a colorless glassy state (57%).

$[\alpha]_D^{28} = -51.5°$ (C=0.20, DMF).

$^1$H—NMR (CDCl$_3$): δ7.23(s, 10H), 7.2–6.7(m, 8H), 5.0–4.3(m, 2H), 4.3–3.8(m, 5H), 3.4–2.6(m, 12H), 1.91(s, 3H), 1.9–1.0(m, 3H), 1.26(t, 3H, J=7 Hz), 1.23(t, 3H, J=7 Hz), 1.0–0.6(m, 6H).

MS (30 eV): m/Z 855 (M+).

EXAMPLE 22

Diethyl ester of N-(N-acetyl-L-isoleucyl-O-stearoyl-L-tyrosyl)-(R)-(−)-1-amino-2-(4-stearoyloxyphenyl)ethylphosphonic acid (22):

In the same manner as in Example 21, 173 mg of the captioned compound in a white waxy state was obtained from diethyl ester of N-(N-acetyl-L-isoleucyl-L-tyrosyl)-(R)-(−)-1-amino-2-(4-hydroxyphenyl)ethylphosphonic acid and stearic acid (26%).

$[\alpha]_D^{28} = -39.4°$; (C=0.218, DMF).

EXAMPLE 23

N-(N-acetyl-L-isoleucyl-O-methyl-L-tyrosyl)-(R)-(−)-1-amino-2-(4-methoxyphenyl)ethylphosphonic acid (23):

At first, 224 μl (1.70 m moles) of trimethylsilyl bromide was added to a solution of 350 mg (0.565 m moles) of the compound 17 in 2 ml of anhydrous chloroform, and the mixture was stirred at room temperature overnight. Then, 0.5 ml of water was added to the reaction mixture, whereby precipitates were formed and the entire solution portion was solidified. The mixture was filtered to remove the filtrate, and the solid was washed with chloroform, water and then ethyl ether (3×2 ml each), and dried under reduced pressure to obtain 296 mg of a light brown powder (93%). The powder was recrystallized from DMF-chloroform to obtain 240 mg of the captioned compound in a light yellow crystalline state (75%).

Melting point: 245.5°–247° C.

$[\alpha]_D^{26} = -83.0°$; (C=0.218, DMF).

$^1$H—NMR (DMSO—d$_6$): δ7.3–6.6(m, 8H), 4.7–3.9(m, 3H), 3.69(s, 6H), 3.3–2.5(m, 4H), 1.9–0.9(m, 3H), 1.83(s, 3H), 0.9–0.5(m, 6H).

EXAMPLE 24

N-(N-acetyl-L-isoleucyl-O-acetyl-L-tyrosyl)-(R)-(−)-1-amino-2-(4-acetoxyphenyl)ethylphosphonic acid (24):

In the same manner as in Example 23, 279 mg of a light brown powder was obtained from the compound 18 (82%). The powder was recrystallized from DMF-chloroform to obtain 188 mg of the captioned compound in a light yellow crystalline state (55%).

Melting point: 232°–234° C.

$[\alpha]_D^{26} = -73.5°$; (C=0.204, DMF).

$^1$H—NMR (DMSO—d$_6$): δ7.4–6.8(m, 8H), 4.7–3.8(m, 3H), 3.5–2.5(m, 4H), 2.24(s, 6H), 1.82(s, 3H), 1.8–0.9(m, 3H), 0.9–0.4(m, 6H).

EXAMPLE 25

N-(N-acetyl-L-isoleucyl-O-benzoyl-L-tyrosyl)-(R)-(−)-1-amino-2-(4-benzoyloxyphenyl)ethylphosphonic acid (25):

In the same manner as in Example 23, 378 mg of a light brown powder was obtained from the compound 19 (90%). The powder was recrystallized from DMF-chloroform to obtain 208 mg of the captioned compound in a light yellow crystalline state (50%).

Melting point: 251°–252° C.

$[\alpha]_D^{26} = -73.6°$ (C=0.212, DMF).

$^1$H—NMR (DMSO—d$_6$): δ8.3–6.9(m, 18H), 4.9–3.8(m, 3H), 3.5–2.5(m, 4H), 1.85(s, 3H), 1.8–1.0(m, 3H), 1.0–0.5(m, 6H).

EXAMPLE 26

N-(N-acetyl-L-isoleucyl-O-pivaloyl-L-tyrosyl)-(R)-(−)-1-amino-2-(4-pivaloyloxyphenyl)ethylphosphonic acid (26):

In the same manner as in Example 23, 191 mg of a light yellow powder was obtained from the compound 20 (52%). The powder was recrystallized from DMF-chloroform to obtain 87 mg of the captioned compound in a white crystalline state (24%).

Melting point: 237°–239° C.

$[\alpha]_D^{26} = -61.8°$ (C=0.212, DMF).

$^1$H—NMR (DMSO—d$_6$): δ7.4–6.7(m, 8H), 4.7–3.7(m, 3H), 3.4–2.5(m, 4H), 1.85(s, 3H), 1.8–1.0(m, 3H), 1.28(s, 18H), 1.0–0.5(m, 6H).

EXAMPLE 27

N-{N-acetyl-L-isoleucyl-O-(3-phenylpropanoyl)-L-tyrosyl}-(R)-(−)-1-amino-2-{4-(3-phenylpropanoyloxy)phenyl}ethylphosphonic acid (27):

In the same manner as in Example 23, 265 mg of a light yellow powder was obtained from the compound 21 (81%). The powder was recrystallized from DMF-chloroform to obtain 156 mg of the captioned compound in a light yellow crystalline state (48%).

Melting point: 237°–238° C.

$[\alpha]_D^{26} = -55.3°$; (C=0.206, DMF).

$^1$H—NMR (DMSO—d$_6$): δ7.5–6.7(m, 18H), 4.7–3.7(m, 3H), 3.4–2.5(m, 12H), 1.85(s, 3H), 1.8–0.9(m, 3H), 0.9–0.5(m, 6H).

EXAMPLE 28

N-(N-acetyl-L-isoleucyl-O-stearoyl-L-tyrosyl)-(R)-(−)-1-amino-2-(4-stearoyloxyphenyl)ethylphosphonic acid (28):

in the same manner as in Example 23, 193 mg of a light yellow powder was obtained from the compound 22 (88%). The powder was recrystallized from DMF-chloroform to obtain 136 mg of the captioned compound in a light yellow crystalline state (62%).

Melting point: 234.5°–235.5° C.

$[\alpha]_D^{26} = -43.8°$ (C=0.21, DMF).

EXAMPLE 29

N-(N-acetyl-L-isoleucyl-O-benzyl-L-tyrosyl)-(R)-(−)-1-amino-2-(4-benzyloxyphenyl)ethylphosphonic acid (29):

In the same manner as in Example 23, 4.16 g of a white solid was obtained from diethyl ester of N-(N-acetyl-L-isoleucyl-O-benzyl-L-tyrosyl)-(R)-(−)-1-amino-2-(4-benzyloxyphenyl)ethylphosphonic acid (92%). The solid was recrystallized from DMF to obtain 2.98 g of the captioned compound in a white crystalline state (66%).

| Elemental analysis: As $C_{39}H_{46}N_3O_8P$ | | |
|---|---|---|
| | Calculated | Found |
| C | 65.44 | 65.43 |
| H | 6.48 | 6.46 |
| N | 5.87 | 6.06 |

Melting point: 259.5°–260° C.

$[\alpha]_D^{26} = -74.8°$; (C=0.202, DMF).

$^1$H—NMR (DMSO—d$_6$): δ7.37(m, 10H), 7.35–6.7(m, 8H), 5.11(s, 4H), 4.7–3.8(m, 3H), 3.4–2.45(m, 4H), 1.81(s, 3H), 1.8–0.9(m, 3H), 0.9–0.5(m, 6H).

IR (KBr): 3300, 1640, 1540, 1510, 1250, 1180, 1015 cm$^{-1}$.

EXAMPLE 30

Diisopropyl ester of N-(N-acetyl-L-isoleucyl-L-tyrosyl)-(R)-(−)-1-amino-2-(4-hydroxyphenyl)ethylphosphonic acid (30):

At first, 1 ml of pyridine, 825 mg (4.0 m moles) of DCC and then 124 μl (1.6 m moles) of isopropanol were added to a solution of 286 mg (0.40 m mole) of the compound 29, in 3 ml of DMF, and the mixture was stirred at room temperature overnight. Then, 0.5 ml of acetic acid and 0.5 ml of water were added to the reaction mixture to decompose excess DCC. Deposited N,N'-dicyclohexylurea was removed therefrom by filtration, and 50 ml of chloroform was added to the filtrate. The resulting solution was washed with an aqueous 5% citric acid solution, an aqueous 5% sodium hydrogen carbonate solution and then an aqueous saturated sodium chloride solution (2×20 ml each) and dried over anhydrous sodium sulfate. The solvent was removed therefrom under reduced pressure to obtain a light yellow solid. Then, 200 mg of 10% palladium-carbon and 5 ml of acetic acid were added to the solid, and the resulting suspension was stirred in a hydrogen gas stream at room temperature overnight. Insoluble matters were removed from the reaction mixture by filtration, and the solvent was removed from the filtrate under reduced pressure to obtain a white solid. The solid was recrystallized from methanol to obtain 88 mg of the captioned compound in a white crystalline state (36%).

| Elemental analysis (%): as C$_{31}$H$_{46}$N$_3$O$_8$P | | |
|---|---|---|
| | Calculated | Found |
| C | 60.08 | 59.98 |
| H | 7.48 | 7.63 |
| N | 6.78 | 6.86 |

Melting point: 280°–281° C. (decomposed).
$[\alpha]_D^{20} = -78.0°$; (C=0.20, DMF).
$^1$H—NMR (CD$_3$OD): δ7.25–6.5(m, 8H), 4.8–4.25 (m, 2H), 4.06(d, 1H, J=8.1 Hz), 3.3–2.4(m, 4H), 1.93(s, 3H), 1.9–1.0(m, 3H), 1.36(d, 6H, J=6.1 Hz), 1.34(d, 6H, J=6.1 Hz), 1.0–0.5(m, 6H).
MS (20 eV): m/Z 619 (M+).

EXAMPLE 31

Dibutyl ester of N-(N-acetyl-L-isoleucyl-L-tyrosyl)-(R)-(−)-1-amino-2-(4-hydroxyphenyl)ethylphosphonic acid (31):

In the same manner as in Example 30, 127 mg of the captioned compound in a white crystalline state was obtained from the compound 29 and 1-butanol (49%).

Melting point: 271°–272° C.
$[\alpha]_D^{20} = -69.7°$ (C=0.208, DMF).
$^1$H-NMR (CD$_3$OD): δ7.2–6.55(m, 8H), 4.8–4.35(m, 2H), 4.2–3.85(m, 5H), 3.25–2.5(m, 4H), 1.93(s, 3H), 1.9–1.0(m, 11H), 1.0–0.6(m, 12H).
MS (20 eV): m/Z 647 (M+).

EXAMPLE 32

Didodecyl ester of N-(N-acetyl-L-isoleucyl-L-tyrosyl)-(R)-(−)-1-amino-2-(hydroxyphenyl)ethylphosphonic acid (32):

In the same manner as in Example 30, 247 mg of the captioned compound in a white crystalline state was obtained from the compound 29 and 1-dodecanol (47%).

Melting point: 252°–254° C.
$[\alpha]_D^{20} = -51.5°$; (C=0.204, DMF).
MS (20 eV): m/Z 871 (M+).

EXAMPLE 33

Dioctadecyl ester of N-(N-acetyl-L-isoleucyl-L-tyrosyl)-(R)-(−)-1-amino-2-(4-hydroxyphenyl)ethylphosphonic acid (33):

In the same manner as in Example 30, 89 mg of the captioned compound in a white powdery state was obtained from the compound 29 and 1-octadecanol (21%).

Melting point: 244°–250° C.
$[\alpha]_D^{20} = -40.9°$; (C=0.208, DMF).

EXAMPLE 34

Di(3,6,9,12-tetraoxatridecyl)ester of N-(N-acetyl-L-isoleucyl-L-tyrosyl)-(R)-(−)-1-amino-2-(4-hydroxyphenyl)ethylphosphonic acid (34):

In the same manner as in Example 30, 224 mg of the captioned compound in a white powdery state was obtained from the compound 29 and 3,6,9,12-tetraoxatridecanol.

Melting point: 200°–202° C.
$[\alpha]_D^{20} = -44.9°$; (C=0.256, DMF).
$^1$H—NMR (CD$_3$OD): δ7.15–6.5(m, 8H), 4.85–4.4(m, 2H), 4.3–3.95(m, 5H), 3.8–3.4(m, 34H), 3.2–2.5(m, 4H), 1.94(s, 3H), 1.9–1.0(m, 3H), 1.0–0.6(m, 6H).

EXAMPLE 35

Di(1,3-dilauroyloxy-2-propyl)ester of N-(N-acetyl-L-isoleucyl-L-tyrosyl)-(R)-(−)-1-amino-2-(4-hydroxyphenyl)ethylphosphonic acid (35):

At first, 822 mg (1.8 m moles) of glycerol α,α'-dilaurate was added to a solution of 429 mg (0.60 m mole) of the compound 29 and 27 mg (2.4 m moles) of 2,4,6-triisopropylbenzenesulphonyl chloride in 3 ml of anhydrous pyridine, and the mixture was stirred for 7 hours. Then, 50 ml of chloroform was added to the reaction mixture, and the resulting solution was washed with an aqueous 5% citric acid solution, an aqueous 5% sodium hydrogen carbonate solution and then an aqueous saturated sodium chloride solution (3×10 ml each), and dried over anhydrous sodium sulfate. The solvent was removed therefrom under reduced pressure to obtain a light yellow solid. The solid was purified by silica gel column chromatography (dichloromethane:ethyl ether=1:3), and the solvent was removed therefrom under reduced pressure to obtain 348 mg of a white solid. Then, 200 mg of 10% palladium-carbon and 5 ml of acetic acid were added to the solid, and the resulting suspension was stirred in a hydrogen gas stream at room temperature overnight. Insoluble matters were removed therefrom by filtration, and the solvent was removed from the filtrate to obtain an oily matter. The oily matter was purified by silica gel column chromatography (chloroform:acetone=5:1) and the solvent was removed therefrom under reduced pressure to obtain 238 mg of the captioned compound in a white waxy state (28%).

$[\alpha]_D^{26} = -31.2°$; (C=0.314, DMF).

EXAMPLE 36

Dimethyl ester of N-(N-acetyl-L-isoleucyl-L-tyrosyl)-(R)-(−)-1-amino-2-(4-hydroxyphenyl)ethylphosphonic acid (36):

A solution of 286 mg (0.40 m mole) of the compound 29 in 10 ml of DMF was stirred under ice cooling, and a solution of diazomethane in ethyl ether was added dropwise thereto until the disappearance of the yellow color of the reaction solution no more took place. Excess diazomethane was decomposed with acetic acid, and the solvent was removed therefrom under reduced pressure to obtain a white solid. Then, 200 mg of 10% palladium-carbon and 10 ml of acetic acid were added to the solid, and the resulting suspension was stirred in a hydrogen gas stream at room temperature overnight. Insoluble matters were removed from the reaction mixture by filtration, and the solvent was removed from the filtrate to obtain a white solid. The solid was recrystallized from methanol-chloroform to obtain 159 mg of the captioned compound in a white crystalline state (71%).

Melting point: 252.2°–254° C.

$[\alpha]_D^{20} = -83.5°$; (C=0.206, DMF).

$^1$H—NMR (CD$_3$OD): δ7.2–6.5(m, 8H), 4.8–4.25(m, 2H), 4.06(d, 1H, J=8.1 Hz), 3.73(d, 3H, J=10.7 Hz), 3.72(d, 3H, J=10.7 Hz), 3.25–2.5(m, 4H), 1.94(s, 3H), 1.9–1.0(m, 3H), 1.0–0.6(m, 6H).

MS (20 eV): m/Z 563 (M+).

EXAMPLE 37

Monoethyl ester of N-(N-acetyl-L-isoleucyl-L-tyrosyl)-(R)-(−)-1-amino-2-(4-hydroxyphenyl)ethylphosphonic acid (37):

At first, 58.4 μl (1.0 m mole) of ethanol was added to a solution of 716 mg (1.0 m mole) of the compound 29 and 363 mg (1.2 m moles) of 2,4,6-triisopropylbenzenesulfonyl chloride in 4 ml of anhydrous pyridine, and the mixture was stirred at room temperature overnight. The solvent was removed from the reaction mixture under reduced pressure, and 10 ml of ethyl acetate and 10 ml of 6N hydrochloric acid were added to the residue to deposit a solid. The solid was collected therefrom by filtration, washed with ethyl acetate, 1N hydrochloric acid, methanol and ethyl ether in this order (3×3 ml each), and dried under reduced pressure to obtain 587 mg of a white powder. Then, 200 mg of 10% palladium-carbon and 10 ml of acetic acid were added to 556 mg of the powder, and the suspension was stirred in a hydrogen gas stream at room temperature overnight. Insoluble matters were removed from the reaction mixture by filtration, and the solvent was removed from the filtrate to obtain 428 mg of a white solid. The solid was purified by silica gel preparative TLC (chloroform:methanol:aqueous ammonia=55:40:5). Then, 6N hydrochloric acid was added to an aqueous solution of the product to form a white precipitate. The precipitate was collected by filtration, washed with water and dried under reduced pressure to obtain 133 mg of the captioned compound in a white powdery state (24%).

Melting point: 253°–257° C.

$[\alpha]_D^{20} = -79.4°$; (C=0.204, DMF).

$^1$H—NMR (CD$_3$OD): δ7.2–6.45(m, 8H), 4.7–4.3(m, 2H), 4.2–3.9(m, 3H), 3.2–2.4(m, 4H), 1.93(s, 3H), 1.9–1.0(m, 3H), 1.30(t, 3H, J=7.1 Hz), 1.0–0.6 (m, 6H).

EXAMPLE 38

Diethyl ester of N-(N-t-butoxycarbonyl-L-isoleucyl-L-phenylalanyl)-(R)-(−)-1-amino-2-(4-benzyloxyphenyl)ethylphosphonic acid (38):

(1) Diethyl ester hydrochloride of N-L-phenylalanyl-(R)-(−)-1-amino-2-(4-benzyloxyphenyl)ethylphosphonic acid:

At first, 7.26 g (20 m moles) of diethyl ester of (±)-1-amino-2-(4-benzyloxyphenyl)ethylphosphonic acid 48 (see Reference Example 3), 5.57 g (21 m moles) of N-t-butoxycarbonyl-L-phenylalanine, and 2.84 g (21 m moles) of 1-hydroxybenzotriazole were dissolved in 30 ml of THF, and then the solution was cooled to about −10° C. in a dry ice-ice bath while stirring the solution. Then, 5 ml of a THF solution containing 4.33 g (21 m moles) of DCC was added dropwise to the solution. The reaction solution was brought to 0° C. over about 2 hours, and then stirred at room temperature overnight. Deposited N,N'-dicyclohexylurea was removed therefrom by filtration, and 100 ml of ethyl acetate was added to the filtrate, and the thus obtained homogeneous solution was washed successively with an aqueous 5% sodium hydrogen carbonate solution, an aqueous 5% citric acid solution, and an aqueous saturated sodium chloride solution (each 3×30 ml). The organic layer was dried over anhydrous sodium sulfate, and the solvent was removed therefrom under reduced pressure to obtain 11.3 g of light yellow powder. Then, 30 ml of ethyl acetate was added to the powder to make a homogeneous solution, and then 150 ml of a 2.6N hydrogen chloride solution in ethyl acetate was added thereto. The mixture was stirred at room temperature for one hour. The solvent and excess hydrogen chloride were removed under reduced pressure to obtain light yellow gum-like substance. The compound gave two spots of R$_f$=0.45 and 0.24 on silica gel TLC (chloroform:methanol=9:1). The substance was subjected to silica gel chromatography and developed with a mixed solvent of chloroform:methanol=96:4. Fractions containing the compound of R$_f$=0.45 were collected, and the solvent was removed therefrom under reduced pressure to obtain 4.01 g (70%) of the captioned compound as a light yellow powder (70%).

$[\alpha]_D^{13} = -36.2°$; (C=1.01, methanol).

$^1$H—NMR (CDCl$_3$): δ7.45–6.7(m, 14H), 4.95(s, 2H), 4.6(m, 1H), 4.02(m, 4H), 3.4–2.6(m, 4H), 1.25(t, 3H, J=7 Hz), 1.20(t, 3H, J=7 Hz).

MS (20 eV): m/z 510 (M+—HCl).

(2) Diethyl ester of N-(N-t-butoxycarbonyl-L-isoleucyl-L-phenylalanyl)-(R)-(−)-1-amino-2-(4-benzyloxyphenyl)ethylphosphonic acid:

At first, 673 mg (2.91 m moles) of N-t-butoxycarbonyl-L-isoleucine, 1.59 g (2.91 m moles) of diethyl ester hydrochloride of N-L-phenylalanyl-(R)-(−)-1-amino-2-(4-benzyloxyphenyl)ethylphosphonic acid, and 413 mg (3.06 m moles) of 1-hydroxybenzotriazole were dissolved in 30 ml of THF, and then the solution was cooled to about −10° C. in a dry ice-ice bath while stirring the solution. Then, 0.336 ml (3.06 m moles) of N-methylmorpholine and then 10 ml of a THF solution containing 631 mg (3.06 m moles) of DCC were added dropwise to the solution. The reaction solution was brought to 0° C. over about 2 hours, and then stirred at room temperature overnight. Deposited N,N'-dicyclohexylurea was removed by filtration, and 100 ml of ethyl acetate was added to the filtrate. The resultant homogenous solution was washed successively with an aqueous 5% sodium hydrogen carbonate solution, an aqueous 5% citric acid solution and an aqueous saturated sodium chloride solution (each 3×30 ml). The organic layer was dried over anhydrous sodium sulfate, and the solvent was removed therefrom under reduced pressure to obtain light yellow solid. The solid was purified by silica gel chromatography (ethyl acetate) and the solvent was removed under reduced pressure to obtain 2.0 g of the captioned compound as a white powder (95%).

| Elemental analysis (%): as $C_{39}H_{54}N_3O_8P$ | | |
|---|---|---|
| | Calculated | Found |
| C | 64.71 | 64.85 |
| H | 7.52 | 7.56 |
| N | 5.81 | 5.63 |

$[\alpha]_D^{22} = -47.6°$; (C=0.50, DMF).
$^1$H—NMR (CDCl$_3$): δ7.5–6.7(m, 14H), 4.96(s, 2H), 4.9–4.4(m, 2H), 4.3–3.7(m, 5H), 3.3–2.6(m, 4H), 1.9–1.0(m, 3H), 1.40(s, 9H), 1.27(t, 3H, J=7 Hz), 1.23(t, 3H, J=7 Hz), 1.0–0.6(m, 6H).

EXAMPLE 39

Diethyl ester of N-(N-acetyl-L-isoleucyl-L-phenylalanyl)-(R)-(—)-1-amino-2-(4-benzyloxyphenyl)ethylphosphonic acid (39):

At first, 182 mg (1.05 m moles) of N-acetyl-L-isoleucin, 547 mg (1.0 m mole) of diethyl ester hydrochloride of N-L-phenylalanyl-(R)-(—)-1-amino-2-(4-benzyloxyphenyl)ethylphosphonic acid, and 142 mg (1.05 m moles) of 1-hydroxybenzotriazole were dissolved in 5 ml of THF, and the solution was cooled to about −10° C. in a dry ice-ice bath while stirring the solution. Then, 0.115 ml (1.05 m moles) of N-methylmorpholine and then 1 ml of a THF solution containing 217 mg (1.05 m moles) of DCC were added dropwise thereto, and the reaction solution was brought to 0° C. over about 2 hours, and then stirred at room temperature overnight. Deposited N,N'-dicyclohexylurea was removed by filtration, and 50 ml of chloroform was added to the filtrate. The resultant homogeneous solution was washed successively with an aqueous 5% sodium hydrogen carbonate solution, an aqueous 5% citric acid solution, and an aqueous saturated sodium chloride solution (each 3×20 ml).

The organic layer was dried over anhydrous sodium sulfate and the solvent was removed therefrom under reduced pressure to obtain 655 mg of white solid. By recrystallization from chloroform-diethyl ether, 554 mg of the captioned compound as white crystal (83%).

Melting point: 194°–197.5° C.
$[\alpha]_D^{16} = -47.8°$; (C=0.478, methanol).
$^1$H—NMR (CDCl$_3$): δ7.33(s, 5H), 7.3–6.7(m, 9H), 4.97(s, 2H), 4.9–4.3(m, 2H), 4.3–3.8(m, 5H), 3.3–2.6(m, 4H), 1.94(s, 3H), 1.9–1.0(m, 3H), 1.27(t, 3H, J=7 Hz), 1.23(t, 3H, J=7 Hz), 1.0–0.6(m, 6H).
MS (30 eV): m/z 665 (M$^+$).
IR (KBr): 3340, 2930, 1640, 1625, 1570, 1240, 1045, 1020, 970 cm$^{-1}$.

EXAMPLE 40

Diethyl ester of N-(N-acetyl-L-isoleucyl-L-alanyl)-(R)-(—)-1-amino-2-(4-benzyloxyphenyl)ethylphosphonic acid (40):

The captioned compound in a white crystal state was obtained from N-acetyl-L-isoleucine and diethyl ester hydrochloride of N-L-alanyl-(R)-(—)-1-amino-2-(4-benzyloxyphenyl)ethylphosphonic acid in the same manner as in Example 39.
Melting point: 199.5°–202.5° C.
$[\alpha]_D^{21} = -38.5°$; (C=0.20, methanol).
MS (20 eV): m/z 590 (M$^+$+1).

EXAMPLE 41

Diethyl ester of N-(N-acetyl-L-isoleucyl-L-isoleucyl)-(R)-(—)-1-amino-2-(4-benzyloxyphenyl)ethylphosphonic acid (41):

The captioned compound in a white crystal state was obtained from N-acetyl-L-isoleucine and diethyl ester hydrochloride of N-L-isoleucyl-(R)-(—)-1-amino-2-(4-benzyloxyphenyl)ethylphosphonic acid in the same manner as in Example 39.
Melting point: 235.0°–236.8° C.
$[\alpha]_D^{16} = -50.0°$; (C=0.504, methanol).

EXAMPLE 42

N-(N-acetyl-L-isoleucyl-L-isoleucyl)-(R)-(—)-1-amino-2-(4-hydroxyphenyl)ethylphosphonic acid (42):

At first, 0.46 ml of anisole and 2 ml of a solution of 25% hydrogen bromide in acetic acid were added to 130 mg of the compound 41, and the mixture was stirred at room temperature for 4 hours. Volatile matters were removed therefrom under reduced pressure to obtain an orange oily substance. Then, 5 ml of ethyl ether was added thereto, the mixture was triturated, and the supernatant was discarded. This operation was repeated five times to obtain an orange solid. By recrystallization from methanol-chloroform, 86 mg of the captioned compound was obtained as light yellow crystal (84%).

| Elemental analysis: as $C_{22}H_{36}N_3O_7P$ | | |
|---|---|---|
| | Calculated | Found |
| C | 54.43 | 54.24 |
| H | 7.47 | 7.54 |
| N | 8.65 | 8.52 |

Melting point: 300° C. or higher.
$[\alpha]_D^{15} = -86.0°$; (C=0.10, methanol).
$^1$H—NMR (D$_2$O—NaOD, DSS, internal standard): δ7.2–6.5(m, 4), 4.12(d, 1H, J=8.3 Hz), 3.99(d, 1H, J=8.9 Hz), 3.3–2.4(m, 2H), 2.01(s, 3H), 1.9–1.0(m, 6H), 1.0–0.4(m, 12H).
IR (KBr): 3280, 2960, 1640, 1550, 1220, 1000 cm$^{-1}$.

EXAMPLE 43

N-(N-acetyl-L-isoleucyl-L-phenylalanyl)-(R)-(—)-1-amino-2-(4-hydroxyphenyl)ethylphosphonic acid (43):

The captioned compound in a light yellow powdery state was obtained from the compound 39 in the same manner as in Example 42.
Melting point: 222° C. (decomposed).
$[\alpha]_D^{21} = -57.9°$; (C=0.20, methanol).

EXAMPLE 44

N-(N-acetyl-L-isoleucyl-L-alanyl)-(R)-(—)-1-amino-2-(4-hydroxyphenyl)ethylphosphonic acid (44):

The captioned compound in a light yellow powdery state was obtained from the compound 40 in the same manner as in Example 42.
Melting point: 222°–224° C.
$[\alpha]_D^{21} = -66.5°$; (C=0.20, methanol).

EXAMPLE 45

N-(N-L-isoleucyl-L-phenylalanyl)-(R)-(—)-1-amino-2-(4-hydroxyphenyl)ethylphosphonic acid (45):

At first, 522 mg of the compound 38 was dissolved in 1.56 ml of anisole and 2 ml of acetic acid, and then 15 ml of a solution of 25% hydrogen bromide in acetic acid was added to the solution. The solution was stirred at room temperature for 5 hours. Volatile matters were removed therefrom under reduced pressure to obtain a light yellow solid. Propylene oxide was added dropwise to a homogeneous solution of the solid in 2 ml of DMF to form white precipitates. The precipitates were separated by filtration, washed with methanol and ethyl ether (each 2×3 ml), and dried under reduced pressure to obtain 272 mg of the captioned compound as a white powder (79%).

Melting point: 278°–281° C. (decomposed).
$[\alpha]_D^{24} = -100.5°$; (C=0.20, 1N NaOH).
$^1$H—NMR (D$_2$O—NaOD, DSS, internal standard): δ7.1–6.4 (m, 8H), 4.62(m, 1H), 4.04(m, 1H), 3.3–2.9(m, 3H), 2.9–2.25(m, 2H), 1.7–0.5(m, 9H).

Reference Example 1

Diethyl ester hydrochloride of N-(O-benzyl-L-tyrosyl)-1-amino-2-(4-benzyloxyphenyl)ethylphosphonic acid {(R)-(—)-isomer: 46a, (S)-(+)-isomer: 46b}:

A solution of 16.77 g (46.1 m moles) of diethyl ester of (±)-1-amino-2-(4-benzyloxyphenyl)ethylphosphonic acid, 18.0 g (48.4 m moles) of N-t-butoxycarbonyl-O-benzyl-L-tyrosine and 6.54 g (48.4 m moles) of 1-hydroxybenzotriazole in 100 ml of THF was cooled to about −10° C. with stirring, and a solution of 9.79 g (48.4 m moles) of DCC in 20 ml of THF was added to the first solution. The reaction solution was brought to 0° C. over about 2 hours, and then stirred at room temperature overnight. The reaction mixture was filtered, and 300 ml of ethyl acetate was added to the filtrate. Then, the solution was washed with an aqueous 5% sodium hydrogen carbonate solution, an aqueous 5% citric acid solution and then an aqueous saturated sodium chloride solution (3×50 ml each), and dried over anhydrous sodium sulfate. The solvent was removed therefrom under reduced pressure to obtain 32.4 g of a gummy material. Then, 273 ml of a 2.6N hydrogen chloride solution in ethyl acetate was added to a solution of 25.5 g of the material in 100 ml of ethyl acetate, and the mixture was stirred at room temperature for one hour. The solvent and excess hydrogen chloride were removed therefrom under reduced pressure to obtain a light yellow gummy material. The material gave two spots at R$_f$=0.61 and 0.37 on silica gel TLC (chloroform:methanol=9:1). The material was separated and purified by silica gel column chromatography (chloroform:methanol=93:7→3:1) to obtain 6.22 g of (R)-(—)-isomer of the captioned compound 46a (27%) and 4.57 g of (S)-(+)-isomer thereof 46b (20%) respectively in a light yellow powder state.

46a: $[\alpha]_D^{22} = -32.8°$; (C=1.10, methanol).
$^1$H-NMR (CDCl$_3$): δ7.34(m, 10H), 7.2–6.7(m, 8H), 4.99(s, 4H), 4.68(m, 1H), 4.12(m, 4H), 3.6–2.6(m, 4H), 2.10(m, 1H), 1.31(t, 3H, J=7.1 Hz), 1.27(t, 3H, J=7.1 Hz).

MS (20 eV): m/Z 616 (M$^+$ —HCl).
46b:
$[\alpha]_D^{22} = +16.4°$; (C=1.10, methanol).

$^1$H-NMR (CDCl$_3$): δ7.37(m, 10H), 7.2–6.7(m, 8H), 5.03(s, 2H), 5.01(s, 2H), 4.67(m, 1H), 4.14(m, 4H), 3.4–2.7(m, 4H), 2.46(m, 1H), 1.31(t, 3H, J=7.1 Hz), 1.29(t, 3H, J=7.1 Hz).

MS (20 eV): m/Z 616 (M$^+$ —HCl).

Reference Example 2

Diethyl ester hydrochloride of N-L-tyrosyl-(R)-(—)-1-amino-2-(4-methoxyphenyl)ethylphosphonic acid (47a):

In the same manner as in Reference Example 1, the captioned compound in a light yellow powdery state was obtained from diethyl ester of (±)-1-amino-2-(4-methoxyphenyl)ethylphosphonic acid and N-t-butoxycarbonyl-L-tyrosine.

$[\alpha]_D^{26} = -41.0°$; (C=0.20, methanol).
$^1$H—NMR (DMSO-d$_6$): δ7.25–6.5(m, 8H), 4.65–3.7(m, 5H), 3.70(s, 3H), 1.23(t, 3H, J=7 Hz), 1.20(t, 3H, J=7 Hz).

MS (20 eV): m/Z 450 (M$^+$ —HCl).

Reference Example 3

Diethyl (±)-1-amino-2-(4-benzyloxyphenyl)ethylphosphonate (48):

The captioned compound was synthesized according to the following reaction equations:

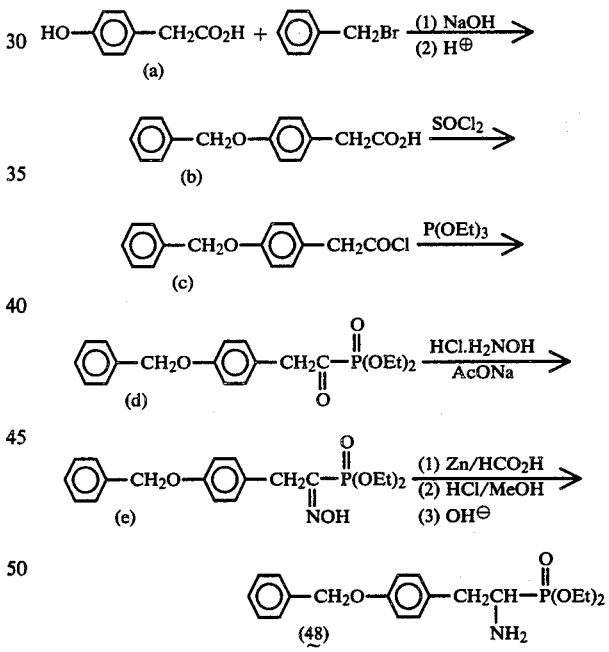

The individual steps are described in detail below:
(1) 4-benzyloxyphenylacetic acid (b):

At first, 291 g (1.91 moles) of 4-hydroxyphenylacetic acid (a) was added to a mixture of 161 g (4.02 moles) of sodium hydroxide, 250 ml of water and 800 ml of ethanol to prepare a homogeneous solution. Then, 240 ml (2.00 moles) of benzyl bromide was added dropwise to the solution at room temperature, and the solution as such was stirred overnight. Deposited white crystal was separated by filtration, washed with 200 ml of concentrated hydrochloric acid and then with 300 ml of water, and dried at 80° C. under reduced pressure to obtain 411 g of white crystal (yield-1). On the other hand, 500 ml of concentrated hydrochloric acid was added to the filtrate, and the resultant white precipitates were separated by filtration, washed with 200 ml of water, and dried at 80° C. under reduced pressure to obtain 50 g of the compound (b) as white crystal (yield-2). Sum of yield-1 and yield-2 was 461 g (99.4%).

Melting point: 121°–123° C.

$^1$H—NMR (CDCl$_3$): δ10.9(bs, 1H), 7.4–6.7(m, 4H), 7.33 (s, 5H), 5.00(s, 2H), 3.53(s, 2H).

(2) Diethyl ester of 4-benzyloxyphenylacetylphosphonic acid (d):

At first, 460 g (1.90 moles) of the compound (b) was added to 800 ml of chloroform dehydrated over P$_2$O$_5$, and then 415 ml (5.70 moles) of thionyl chloride was added dropwise thereto. The mixture was stirred at room temperature for 3 hours, and then volatile matters were removed therefrom under reduced pressure to obtain the compound (c) as a light yellow oily substance. The substance was used as such in the subsequent reaction. A portion of the oily substance was washed with n-hexane and dried under reduced pressure to obtain white crystal.

Compound (c):

Melting point: 71°–73.5° C.

$^1$H—NMR (CDCl$_3$): δ7.4–6.7(m, 4H), 7.35(s, 5H), 5.00(s, 2H), 4.00(s, 2H).

Then, a solution of the compound (c) in 500 ml of toluene was stirred in an ice bath in a nitrogen atmosphere, and then 425 ml (2.47 moles) of triethyl phosphite was added dropwise thereto. Temperature of the reaction solution was returned to room temperature over 3 hours. Then, 1,000 ml of n-hexane was added to the reaction solution, whereby white crystal was precipitated. The crystal was separated by filtration, washed with 2,000 ml of n-hexane, and dried under reduced pressure to obtain 465 g of the compound (d) as white crystal (67.4%).

Melting point 111.5°–113° C.

$^1$H—NMR (CDCl$_3$): δ7.8–6.7(m, 4H), 7.33(s, 5H), 6.00(d, 1H, J=12 Hz), 5.03(s, 2H), 4.17(m, 4H), 1.33(t, 6H, J=7 Hz).

(3) Diethyl ester oxime of 4-benzyloxyphenylacetylphosphonic acid (e):

At first, 1,200 ml of ethanol and 400 ml of water were added to 428 g (1.18 moles) of the compound (d) in a nitrogen atmosphere to prepare a homogeneous solution. Then, 101 g (1.45 moles) of hydroxylamine hydrochloride and 373 g (2.74 moles) of sodium acetate trihydrate were added thereto, and the mixture was stirred at room temperature overnight. The reaction mixture was concentrated under reduced pressure to about 1,000 ml, and extracted with ethyl ether (3×300 ml). The ethyl ether layer was washed successively with an aqueous 5% sodium hydrogen carbonate solution and an aqueous saturated sodium chloride solution (each 2×100 ml), and dried over anhydrous sodium sulfate. The solvent was removed therefrom under reduced pressure to obtain 441 g of the compound (a) as an orange oily substance (99.1%).

$^1$H—NMR (CDCl$_3$): δ7.30(s, 5H), 7.3–6.7(m, 4H), 4.98(s, 2H), 4.4–3.4(m, 6H), 1.17(t, 6H, J=7 Hz).

(4) Diethyl ester of (±)-1-amino-2-(4-benzyloxyphenyl)ethylphosphonic acid (48):

At first, 441 g (1.17 moles) of the compound (e) was dissolved in 600 ml of formic acid, and the solution was stirred under ice cooling. Then, 350 g of zinc powder was added to the solution by portions in such a degree that the temperature of the reaction mixture might not exceed 70° C. Then, the mixture was stirred at room temperature overnight. Insoluble matters in the reaction mixture were removed by filtration, and the filtrate was concentrated under reduced pressure. Then, 500 ml of ethyl acetate and 300 ml of an aqueous saturated sodium chloride solution were added to the concentrated residue to make two layers. The organic layer was collected, washed successively with an aqueous 1N sodium hydroxide solution and an aqueous saturated sodium chloride solution (each 3×300 ml), and dried over anhydrous sodium sulfate. Then, the solvent was removed therefrom under reduced pressure to obtain 400 g of light yellow oily substance. The substance was found by NMR to be a mixture of the desired Compound 48 and N-formyl derivative of 48, and thus the following deformylation and purification were carried out.

At first, solution of 400 g of the oily substance in 200 ml of methanol was added to 800 ml of methanol saturated with hydrogen chloride, and the mixture was stirred at room temperature overnight. Volatile matters were removed from the reaction mixture under reduced pressure, and 500 ml of ethyl acetate and 300 ml of an aqueous saturated sodium chloride solution were added to the residue to make two layers. The organic layer was collected, washed successively with an aqueous 1N sodium hydroxide solution (3×500 ml) and an aqueous saturated sodium chloride solution (2×250 ml), and dried over anhydrous sodium sulfate. The solvent was removed therefrom under reduced pressure. Then, 300 ml of ethyl ether was added to the residue, and the mixture was left standing at −20° C., whereby white crystal was deposited. The crystal was separated by filtration, washed with cold ethyl ether (3×150 ml), and dried under reduced pressure to obtain 269 g of Compound 48 as white crystal (63.3%). Total yield from the compound (a) was 42.0%.

| Elemental analysis (%): as C$_{19}$H$_{26}$NO$_4$P | | |
|---|---|---|
| | Calculated | Found |
| C | 62.80 | 62.65 |
| H | 7.21 | 7.31 |
| N | 3.85 | 3.86 |

Melting point: 71.5°–72.5° C.

$^1$H—NMR (CDCl$_3$): δ7.38(m, 5H), 7.2–6.8(m, 4H), 5.04(s, 2H), 4.16(m, 4H), 3.19(m, 2H), 2.63(m, 1H), 1.34(t, 6H, J=7.0 Hz).

MS (20 eV): m/z (relative intensity) 363(M$^+$, 9), 346(7), 226(37), 198(57), 166(100), 138(15), 91(28).

IR (KBr): 3400, 3000, 1610, 1510, 1240, 1235, 1055, 1030, 970, 945 cm$^{-1}$.

What is claimed is:

1. A compound of the formula

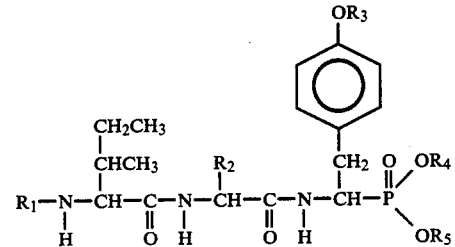

wherein
R$_1$ is hydrogen, lower alkyl, lower alkoxycarbonyl, aralkyloxycarbonyl or

wherein $R_6$ is hydrogen, alkyl having 1 to 17 carbon atoms, unsubstituted or substituted phenyl, naphthyl or biphenyl wherein the substituent is selected from lower alkyl, lower alkoxy and halogen, unsubstituted or substituted aralkyl wherein the substituent is selected from lower alkyl, lower alkoxy and halogen, or cycloalkyl having 5 or 6 carbon atoms;

$R_2$ is unsubstituted or substituted phenyl, naphthyl or biphenyl wherein the substituent is selected from amino, hydroxyl, lower alkoxy, aralkyloxy, lower alkyl, halogen and nitro, unsubstituted or substituted aralkyl wherein the substituent is selected from amino, lower alkyl, halogen and nitro, or

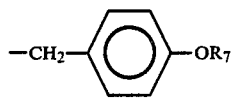

wherein $R_7$ has the same meaning as $R_3$;

$R_3$ is hydrogen, lower alkyl, unsubstituted or substituted aralkyl wherein the substituent has the same meaning as in $R_6$, $R_8$—CO— wherein $R_8$ has the same meaning as $R_6$, $R_9$—O—CO— wherein $R_9$ is lower alkyl, unsubstituted or substituted phenyl, naphthyl or biphenyl wherein the substituent has the same meaning as in $R_6$, unsubstituted or substituted aralkyl wherein the substituent has the same meaning as in $R_6$, or $R_9$NHCO— wherein $R_9$ has the same meaning as defined above; and $R_4$ and $R_5$ are the same or different, and are hydrogens, alkyls having 1 to 18 carbon atoms, unsubstituted or substituted phenyl, naphthyl or biphenyl wherein the substituent has the same meaning as in $R_6$, unsubstituted or substituted aralkyl wherein the substituent has the same meaning as in $R_6$, —$(CH_2CH_2O)_mCH_3$ wherein m is an integer of 1–4, or —$CH[CH_2OCO(CH_2)_nCH_3]_2$ wherein n is 0 or an integer of 1–10 with the proviso that $R_3$, $R_4$ and $R_5$ cannot each be hydrogen when $R_1$ is $CH_3C(O)$— and $R_2$ is

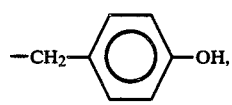

and pharmcologically acceptable salts thereof.

2. A compound according to claim 1, wherein $R_1$ is hydrogen, lower alkoxycarbonyl or

wherein $R_6$ has the same meaning as defined above; $R_2$ is unsubstituted aralkyl or

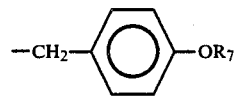

wherein $R_7$ has the same meaning as defined above; $R_3$ is hydrogen, lower alkyl, unsubstituted aralkyl or $R_8$—CO wherein $R_8$ has the same meaning as defined above; and $R_4$ and $R_5$ are the same or different and are hydrogens, alkyls having 1 to 18 carbon atoms, —$(CH_2CH_2O)_mCH_3$ wherein m has the same meaning as defined above or —$CH[CH_2OCO(CH_2)_nCH_3]_2$ wherein n has the same meaning as defined above.

3. A compound according to claim 2, wherein $R_6$ is hydrogen, alkyl having 1 to 17 carbon atoms, unsubstituted phenyl, naphthyl or biphenyl or unsubstituted aralkyl.

4. A compound according to claim 2, wherein Rhd 7 is hydrogen, lower alkyl, unsubstituted aralkyl or $R_8$—CO— wherein $R_8$ has the same meaning as defined above.

5. A compound according to claim 4, wherein $R_8$ is alkyl having 1 to 17 carbon atoms, unsubstituted phenyl, naphthyl or biphenyl or unsubstituted aralkyl.

6. A compound according to claim 2, wherein $R_8$ is alkyl having 1 to 17 carbon atoms, unsubstituted phenyl, naphthyl or biphenyl or unsubstituted aralkyl.

7. A compound according to claim 1, wherein the carbons to which —$CH(CH_3)CH_2CH_3$, $R_2$ and

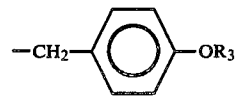

are bonded have optically active configurations respectively.

8. A compound according to claim 7, wherein the carbons to which —$CH(CH_3)CH_2CH_3$ and $R_2$ are bonded have S-configurations respectively, and the carbon to which

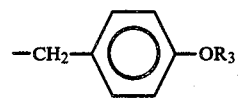

is bonded has R-configuration.

* * * * *

UNITED STATES PATENT AND TRADEMARK OFFICE
CERTIFICATE OF CORRECTION

PATENT NO. : 4,677,125
DATED : June 30, 1987
INVENTOR(S) : MASAYUKI TERANISHI, ET AL.

It is certified that error appears in the above-identified patent and that said Letters Patent is hereby corrected as shown below:

Column 10, line 11, "$OR'_3$" should read --$\overset{\shortmid}{O}R'_3$--.

Column 10, line 15, "$OR'_3$" should read --$\overset{\shortmid}{O}R'_3$--.

Column 12, line 24, "$R'_4 \; R'_5$" should read --$R'_4$ and $R'_5$--.

Column 15, line 33, "$[\alpha]_D^\infty$" should read --$[\alpha]_D^{28}$--.

Column 29, line 57, "(a)" should read --(e)--.

Column 31, line 56, "pharmcologically" should read --pharmacologically--.

Column 32, line 26, "Rhd 7" should read --$R_7$--.

Signed and Sealed this

Seventeenth Day of November, 1987

Attest:

DONALD J. QUIGG

Attesting Officer                  Commissioner of Patents and Trademarks